United States Patent
Ciabatti et al.

(10) Patent No.: US 7,169,890 B2
(45) Date of Patent: Jan. 30, 2007

(54) PROCESS FOR THE PRODUCTION OF RAMOPLANIN-LIKE AMIDE DERIVATIVES

(75) Inventors: Romeo Ciabatti, Novate Milanese (IT); Sonia Maffioli, Milan (IT); Anna Checchia, Bovisio Masciago (IT); Gabriella Romano, Legnano (IT); Gianpaolo Candiani, Gorgonzola (IT); Gianbattista Panzone, Cornaredo (IT)

(73) Assignee: Vicuron Pharmaceuticals Inc., King of Prussia, PA (US)

( * ) Notice: Subject to any disclaimer, the term of this patent is extended or adjusted under 35 U.S.C. 154(b) by 194 days.

(21) Appl. No.: 10/505,881

(22) PCT Filed: Feb. 26, 2003

(86) PCT No.: PCT/EP03/01961

§ 371 (c)(1),
(2), (4) Date: Sep. 3, 2004

(87) PCT Pub. No.: WO03/076460

PCT Pub. Date: Sep. 18, 2003

(65) Prior Publication Data

US 2005/0106691 A1    May 19, 2005

(30) Foreign Application Priority Data

Mar. 8, 2002    (EP) ................................. 02005408

(51) Int. Cl.
*C07K 11/02*    (2006.01)

(52) U.S. Cl. ........................ 530/322; 530/317; 514/23; 514/9

(58) Field of Classification Search .................... None
See application file for complete search history.

(56) References Cited

U.S. PATENT DOCUMENTS 4,328,316 A    5/1982    Cavalleri et al.
5,539,087 A *  7/1996    Restelli et al. .............. 530/412
6,720,305 B1   4/2004    Parenti et al.

FOREIGN PATENT DOCUMENTS

EP    318 680    6/1989

OTHER PUBLICATIONS

Boger DL, "Vancomycin, Teicoplanin, and Ramoplanin: Synthetic and Mechanistic Studies" 2001, Medicinal Research Reviews, vol. 21(5), pp. 356-381.*
Jiang et al., "Total Synthesis of the Ramoplanin A2 and Ramoplanose Aglycon" Jan. 2003, J. Am. Chem. Soc., vol. 125, pp. 1877-1887.*
Degradation, and synthesis of semi synthetic analogs, of the natural antibiotic Ramoplanin, Anno Accademico 2000-2001, pp. 2-66.

* cited by examiner

*Primary Examiner*—Anish Gupta
*Assistant Examiner*—Hemant Khanna
(74) *Attorney, Agent, or Firm*—J. Michael Dixon; Charles W. Ashbrook

(57) ABSTRACT

The invention regards a process for the production of ramoplanin-like derivatives of formula (I): RAMO-NC—CO—R (I), wherein the radical R represents a hydrocarbon radical and the portion RAMO-NH— represents deacylated ramoplanin, any of its factors or ramoplanose. The compound of Formula (I) are obtained by reacting a carboxylic acid R—COOH with deacylated ramoplanin, any of its factors or ramoplanose protected on the ornitine amino groups. New compounds wherein the hydrocarbon radical R is different form those characaterizing the ramoplanin and ramoplanose natural products and their tetrahydro-derivatives are calimed. The new compounds have the same or better antinfective activity, lower haemolytic effect and better tolerability profile than ramoplanin.

11 Claims, No Drawings

PROCESS FOR THE PRODUCTION OF RAMOPLANIN-LIKE AMIDE DERIVATIVES

The object of this invention is to provide a process for the production of ramoplanin-like amide derivatives of the formula (I)

RAMO-NH—CO—R        (I)

where R has the following meanings:
i) a hydrocarbon radical of the formula:

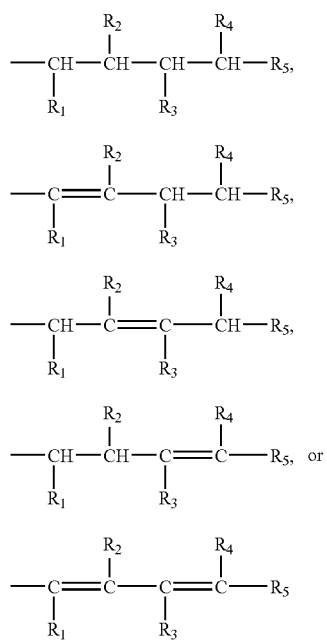

wherein $R_1$, $R_2$ and $R_3$ each independently represents hydrogen, or a lower alkyl of 1 to 4 carbon atoms; $R_4$ represents hydrogen, methyl or ethyl; $R_5$ represents hydrogen or a lower alkyl of 1 to 5 carbon atoms; or ii) a radical of the formula -A-$R_6$ wherein A represents a bond directly connecting the radical $R_6$ with the carbonyl group or a linear or branched ($C_1$–$C_4$)alkylene or ($C_2$–$C_4$) alkylidene radical which may optionally contain a double bond and $R_6$ represents:
  an alkoxy radical of 1 to 4 carbon atoms wherein the alkyl portion may be linear or branched and may optionally contain a double bond and be substituted by 1 to 3 halogen atoms,
  a phenyl radical optionally substituted by 1 to 3 substituents independently selected from halo, cyano, nitro, lower alkyl of 1 to 4 carbon atoms optionally substituted by 1 to 3 halogen atoms, lower alkoxy of 1 to 4 carbon atoms optionally substituted by 1 to 3 halogen atoms, lower alkylthio of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl-lower alkyl, phenoxy and phenoxy-lower alkyl group is optionally substituted by 1 to 3 substituents selected from halo, cyano, nitro, lower alkyl of 1 to 4 carbon atoms optionally substituted by 1 to 3 halogen atoms, lower alkoxy of 1 to 4 carbon atoms optionally substituted by 1 to 3 halogen atoms, and lower alkylthio of 1 to 4 carbon atoms optionally substituted by 1 to 3 halogen atoms,
  a naphthyl radical optionally substituted by one or two substituents selected from halo, lower alkyl of 1 to 4 carbon atoms optionally substituted by 1 to 3 halogen atoms, and lower alkoxy of 1 to 4 carbon atoms optionally substituted by 1 to 3 halogen atoms,
  a phenoxy radical wherein the phenyl portion is optionally substituted by 1 to 3 substituents selected from halo, cyano, nitro, lower alkyl of 1 to 4 carbon atoms optionally substituted by 1 to 3 halogen atoms, lower alkoxy of 1 to 4 carbon atoms optionally substituted by 1 to 3 halogen atoms, and lower alkylthio of 1 to 4 carbon atoms optionally substituted by 1 to 3 halogen atoms, or
  a naphthoxy radical wherein the naphthyl portion is optionally substituted by one or two substituents selected from halo, lower alkyl of 1 to 4 carbon atoms optionally substituted by 1 to 3 halogen atoms, and lower alkoxy of 1 to, 4 carbon atoms optionally substituted by 1 to 3 halogen atoms;
with the proviso that when A represents a bond directly connecting the radical $R_6$ with the cabonyl group, then $R_6$ may not represent a lower alkoxy, a phenoxy or a naphtoxy radical either unsubstituted or optionally substituted as specified above;
the group RAMO-NH— represents the ramoplanin antibiotic core portion of formula (f)

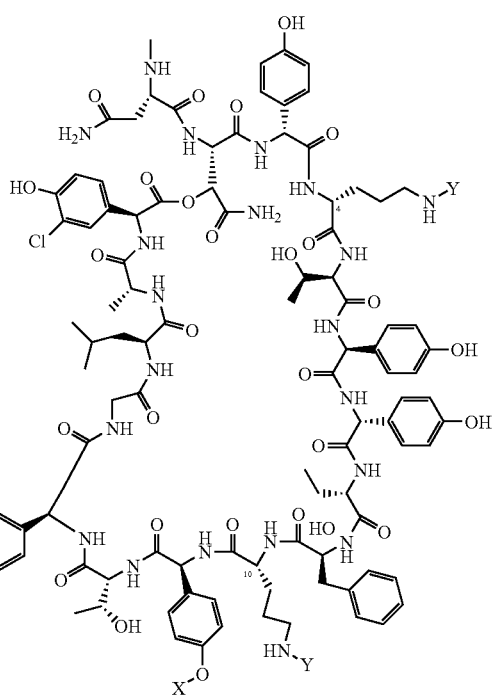

wherein
X represents hydrogen, alpha-D-mannopyranosyl, 2-O-alpha -D-mannopyranosyl-alpha-D-mannopyranosyl or 2,3-O-di[alpha-D-mannopyranosyl]-alpha-D-mannopyranosyl; and
Y represents hydrogen or a protecting group of the amino function;
and the acid addition salts thereof.

A further object of the present invention is to provide novel ramoplanin-like amide derivatives formula (Ia)

RAMO-NH—CO—R        (Ia)

where R has the following meanings:
i) a hydrocarbon radical of the formula:

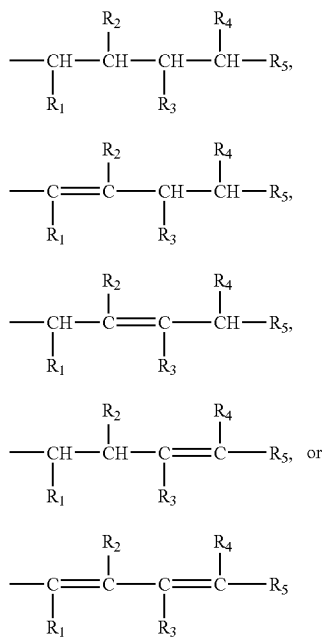

wherein $R_1$, $R_2$ and $R_3$ each independently represents hydrogen, or a lower alkyl of 1 to 4 carbon atoms; $R_4$ represents hydrogen, methyl or ethyl; $R_5$ represents hydrogen or a lower alkyl of 1 to 5 carbon atoms, with the proviso that when R represent a hydrocarbon radical of formula (a) wherein $R_1$, $R_2$, $R_3$ and $R_4$ simultaneously represent hydrogen or of formula (e) wherein $R_1$, $R_2$, $R_3$ and $R_4$ simultaneously represent hydrogen and the double bonds have 2 cis (Z) and 4 trans (E) configuration, respectively, then $R_5$ cannot represent a n-propyl, isobutyl or isopentyl group; or ii) a radical of the formula -A-$R_6$ wherein A represents a bond directly connecting the radical $R_6$ with the carbonyl group or a linear or branched ($C_1$–$C_4$) alkylene or ($C_2$–$C_4$) alkylidene radical which may optionally contain a double bond and $R_6$ represents:

an alkoxy radical of 1 to 4 carbon atoms wherein the alkyl portion may be linear or branched and may optionally contain a double bond and be substituted by 1 to 3 halogen atoms, a phenyl radical optionally substituted by 1 to 3 substituents independently selected from halo, cyano, nitro, lower alkyl of 1 to 4 carbon atoms optionally substituted by 1 to 3 halogen atoms, lower alkoxy of 1 to 4 carbon atoms optionally substituted by 1 to 3 halogen atoms, lower alkylthio of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by 1 to 3 substituents selected from halo, cyano, nitro, lower alkyl of 1 to 4 carbon atoms optionally substituted by 1 to 3 halogen atoms, lower alkoxy of 1 to 4 carbon atoms optionally substituted by 1 to 3 halogen atoms, and lower alkylthio of 1 to 4 carbon atoms optionally substituted by 1 to 3 halogen atoms, a naphthyl radical optionally substituted by one or two substituents selected from halo, lower alkyl of 1 to 4 carbon atoms optionally substituted by 1 to 3 halogen atoms, and lower alkoxy of 1 to 4 carbon atoms optionally substituted by 1 to 3 halogen atoms, a phenoxy radical wherein the phenyl portion is optionally substituted by 1 to 3 substituents selected from halo, cyano, nitro, lower alkyl of 1 to 4 carbon atoms optionally substituted by 1 to 3 halogen atoms, lower alkoxy of 1 to 4 carbon atoms optionally substituted by 1 to 3 halogen atoms, and lower alkylthio of 1 to 4 carbon atoms optionally substituted by 1 to 3 halogen atoms, or a naphthoxy radical wherein the naphthyl portion is optionally substituted by one or two substituents selected from halo, lower alkyl of 1 to 4 carbon atoms optionally substituted by 1 to 3 halogen atoms, and lower alkoxy of 1 to 4 carbon atoms optionally substituted by 1 to 3 halogen atoms, with the proviso that when A represents a bond directly connecting the radical $R_6$ with the carbonyl group, then $R_6$ may not represent a lower alkoxy, phenoxy or a naphthoxy radical either unsubstituted or optionally substituted as specified above;

the group RAMO-NH— represents the ramoplanin antibiotic core portion of formula (f)

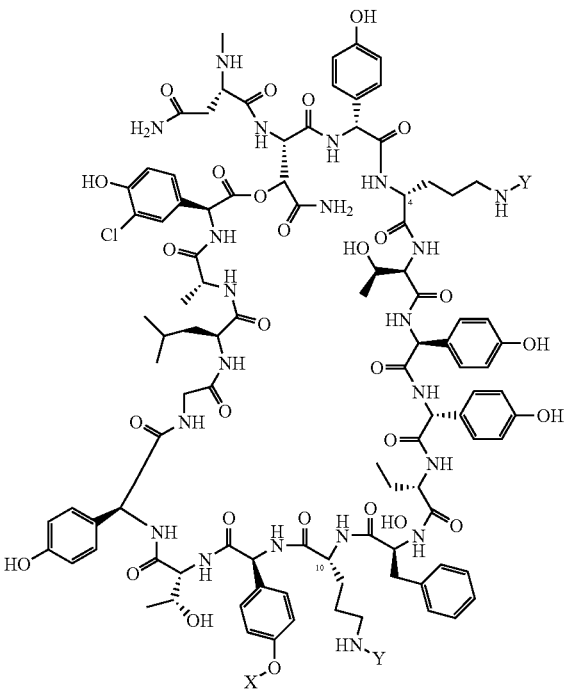

wherein
X represents hydrogen, alpha-D-mannopyranosyl, 2-O-alpha-D-mannopyranosyl-alpha-D-mannopyranosyl or 2,3-O-di[alpha-D-mannopyranosyl]-alpha-D-mannopyranosyl; and Y represents hydrogen or a protecting group of the amino function;

and the acid addition salts thereof.

The above core portion "RAMO-NH" derives from the ramoplanin antibiotics which comprise the ramoplanin factors and ramoplanose.

Ramoplanin (INN, see USP Dictionary of USAN and International Drug Names, 1995) is a known member of the cyclic peptide antibiotics more precisely known as glycolipodepsipeptides which has been described in U.S. Pat. Nos. 4,303,646 and 4,328,316. Originally it has been named antibiotic A 16686. It is a complex substance whose separate factors $A_1$, $A_2$ and $A_3$ have been described in U.S. Pat. No. 4,427,656.

Ramoplanin factors $A'_1$, $A'_2$ and $A'_3$ have been described in EP-B-318680. The aglycones of any of the above factors have been described in EP-B-0337203. A method for selectively increasing the ratio of single major components $A_2$ and $A_3$ is described in EP-B-0259780.

The structure of ramoplanin and its factors and derivatives have been described in several articles and publications, see R. Ciabatti et al., J. Antib. 1989, 42, 254–267, J. K. Kettenring et al., J. Antib 1989, 42, 268–275, R. Ciabatti and B. Cavalleri, Bioactive Metabolites from Microorganisms, Elsevier Science Publishers, 1989, 205–219 and M. Kurz and W. Guba, Biochemistry 1996, 35, 12570–12575.

N. J. Skelton et al. in J. Am. Chem. Soc. 1991, 113, 7522–7530 describe another member of this family, which they call ramoplanose.

The above mentioned ramoplanin antibiotics can be represented by the following formula (II):

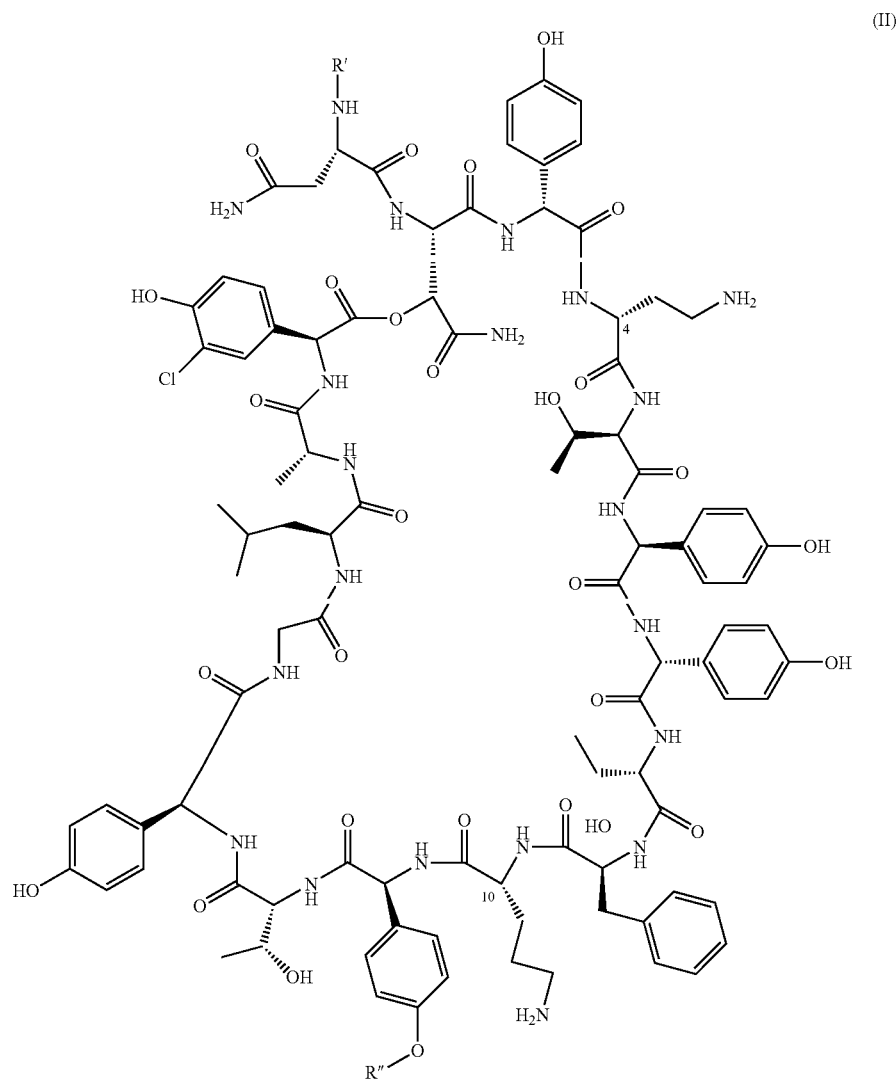

wherein:

R' represents: —CO—CH=CH—CH=CH—CH$_2$—CH$_2$—CH$_3$, —CO—CH=CH—CH=CH—CH$_2$—CH(CH$_3$)$_2$, —CO—CH=CH—CH=CH—CH$_2$—CH$_2$—CH(CH$_3$)$_2$, R" represents: hydrogen, alpha-D-mannopyranosyl or 2-O-alpha-D-mannopyranosyl-alpha-D-mannopyranosyl, or R" represents: 2,3-O-di-[alpha-D-mannopy-ranosyl]-alpha-D-mannopyranosyl when R' represents —CO—CH=CH—CH=CH—CH$_2$—CH(CH$_3$)$_2$ The configuration of the double bonds of the unsaturated moieties reported above in the definition of R' have been found to be 2(Z) or cis and 4(E) or trans, respectively, in the literature reported above.

The following table specifies the meanings for R' and R" of the single factors of ramoplanin with reference to the above formula (II):

| Factor | R' | R" |
|---|---|---|
| $A_1$ | —CO—CH=CH—CH=CH—CH$_2$—CH$_2$—CH$_3$ | 2-O-alpha-D-manno-pyranosyl-alpha-D-mannopyranosyl |
| $A_2$ | —CO—CH=CH—CH=CH—CH$_2$—CH(CH$_3$)$_2$ | 2-O-alpha-D-manno-pyranosyl-alpha-D-mannopyranosyl |
| $A_3$ | —CO—CH=CH—CH=CH—CH$_2$—CH$_2$—CH(CH$_3$)$_2$ | 2-O-alpha-D-manno-pyranosyl-alpha-D-mannopyranosyl |
| $A'_1$ | —CO—CH=CH—CH=CH—CH$_2$—CH$_2$—CH$_3$ | Alpha-D-mannopyranosyl |
| $A'_2$ | —CO—CH=CH—CH=CH—CH$_2$—CH(CH$_3$)$_2$ | Alpha-D-mannopyranosyl |
| $A'_3$ | —CO—CH=CH—CH=CH—CH$_2$—CH$_2$—CH(CH$_3$)$_2$ | Alpha-D-mannopyranosyl |

The aglycones correspond to the compounds of formula (II) reported above wherein R" represents hydrogen.

Ramoplanose is reported to correspond to "factor $A_2$" wherein R" represents 2,3-O-di[alpha-D-mannopyranosyl]-alpha-D-mannopyranosyl.

In addition to the natural compounds designated through formula (II) above, other semisynthetic derivatives related thereto have been described in U.S. Pat. No. 5,708,988. Said compounds correspond to the tetrahydrogenated (in the R' moiety) derivatives of any of the above mentioned ramoplanin factors $A_1$, $A_2$, $A_3$, $A'_1$, $A'_2$ and $A'_3$. The tetrahydrogenated derivatives of the aglycones are described in EP-B-0337203.

All the above compounds are collectively referred in this application and claims as "ramoplanin family".

As it can be easily understood from the meanings of the symbols R and RAMO NH— in formula (I) and of the symbols R' and R" in formula (II) above, the process of this invention besides comprising the method of manufacture of the novel compounds of formula (Ia) provides also a new method of manufacture of each of the above mentioned members of the ramoplanin family.

In the description of this application and claims the term "lower alkyl of 1 to 4 carbon atoms" identifies a methyl, ethyl, propyl, isopropyl, n-butyl, 1-methylpropyl, 2-methylpropyl or tert-butyl group; the term "halo" or "halogen atom" identifies a bromo, cloro or fluoro group; the term "linear or branched ($C_1$–$C_4$) alkylene or ($C_2$–$C_4$)alkylidene radical which may optionally contain a double bond" identifies one of the following groups:

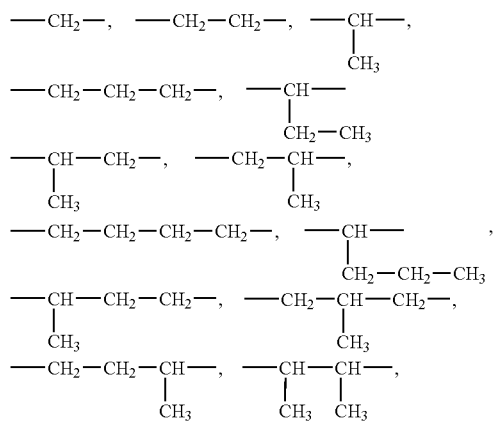

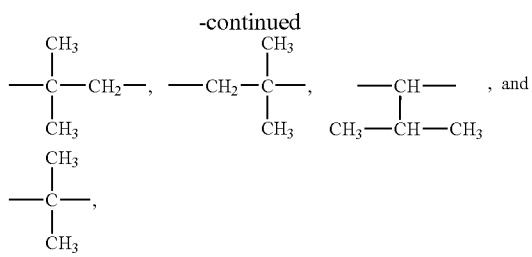

or the corresponding groups containing a double bond between two adjacent carbon atoms, such as

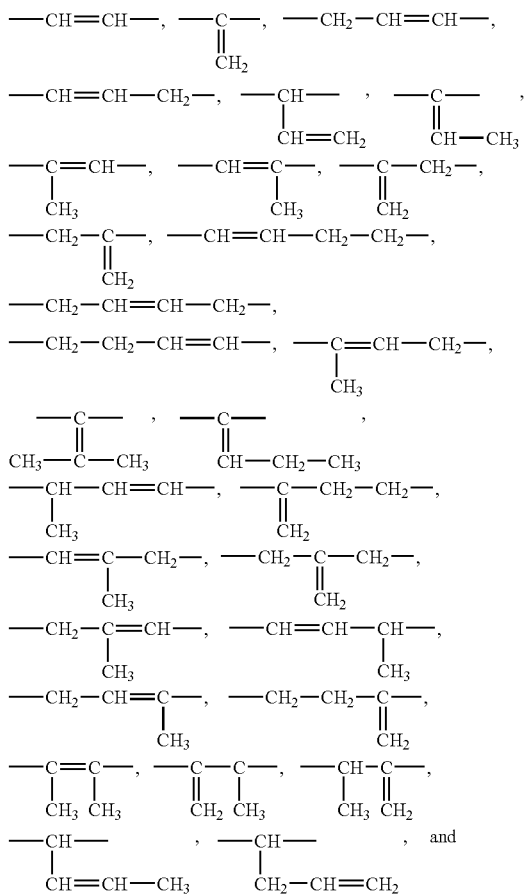

-continued

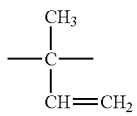

The term "lower alkyl of 1 to 5 carbon atoms" identify a linear or branced alkyl radical which besides those exemplified above includes also the following:

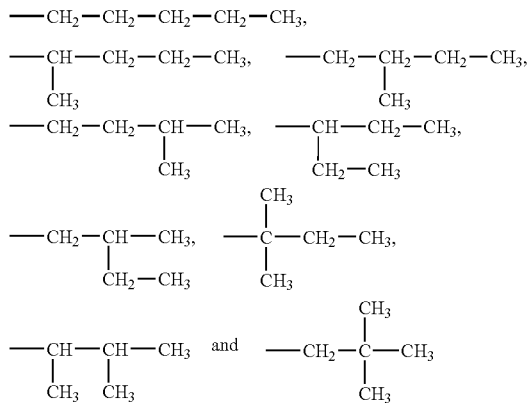

In all cases wherein the radical represented by the symbol R in formula (I) and (Ia) contains one or more asymmetric centers, all possible optical isomers and mixture thereof are comprised within the object of this invention.

Unless otherwise specified, in all cases wherein the radical represented by the symbol R in formula (I) and (Ia) contains double bond(s), both the single isomers presenting the cis (Z) or trans (E) configuration of said double bond(s) and their mixture are falling within the scope of this invention.

In the most current practice, and in this specification, with the generic term "ramoplanin" is intended a complex antibiotic containing major amount of factor $A_2$ (generally more than 75%) accompanied by the other factors described above.

In the description of this application and claims the antibiotic core portion RAMO-NH derives from de-acylation of any member of the ramoplanin family or a mixture thereof. De-acylation means that the radical R' of formula (II) is substituted by hydrogen.

In both formula (I), (Ia) and (II) above the numbers 4 and 10 have been evidenced on the ring carbon atoms pertaining to the two ornithine amino acid residues whose position in the ramoplanin cyclic peptide is conventionally designated as position 4 and position 10, respectively.

The novel compounds of formula (Ia) of this invention, besides exhibiting in most cases an antimicrobical activity of the same level as, and in some cases even better than, that of the prior art compounds pertaining to the ramoplanin family, show better tolerability with respect to said prior art compounds when injected sub-cutaneusly or intravenously in test animals at therapeutically effective dosages.

Among the novel compounds of formula (Ia) of this invention are preferred those compounds wherein R represents:

i) a hydrocarbon radical of formula (a), (b), (c), (d) or (e) above, wherein $R_1$, $R_2$, and $R_3$ each independently represents hydrogen, methyl, ethyl or propyl, $R_4$ represents hydrogen, methyl or ethyl, $R_5$ represents hydrogen or lower-alkyl of 1 to 4 carbon atoms, with the proviso that the total number of carbon atom of said radical (a), (b), (c), (d) or (e) is between 4 and 8, inclusive, and with the further proviso that when R represents a hydrocarbon of formula (a) wherein $R_1$, $R_2$, $R_3$ and $R_4$ simultaneously represent hydrogen or of formula (e) wherein $R_1$, $R_2$, $R_3$ and $R_4$ simultaneously represent hydrogen and the double bonds have 2 cis (Z) and 4 trans (E) configuration, respectively, then $R_5$ cannot represent a lower-alkyl of 3 or 4 carbon atoms, or ii) a radical of the formula -A-$R_6$ wherein A represents a bond directly connecting the radical $R_6$ with the carbonyl group or a linear or branched ($C_1$–$C_4$) alkylene or ($C_2$–$C_4$) alkylidene radical which may optionally contain a double bond and $R_6$ represents:

a phenyl radical optionally substituted by 1 to 3 substituents selected from lower alkyl of 1 to 4 carbon atoms, trifluoromethyl, lower alkoxy of 1 to 4 carbon atoms, trifluoromethoxy, trifluoromethylthio, chloro, bromo, fluoro, nitro, cyano and phenyl, a naphthyl radical optionally substituted by one or two substituents selected from lower alkyl of 1 to 4 carbon atoms, lower alkoxy of 1 to 4 carbon atoms, chloro, fluoro, trifluoromethyl and trifluoromethoxy, or a phenoxy radical, optionally susbtituted with a lower alkyl of 1 to 4 carbon atoms;

with the proviso that when A represents a bond directly connecting the radical $R_6$ with the carbonyl group, then $R_6$ may not represent phenoxy or phenoxy optionally substituted with a lower alkyl of 1 to 4 carbon atoms;

the group RAMO-NH— represents the ramoplanin antibiotic core portion of formula (f) above wherein X represents hydrogen, 2-alpha-D-mannopyranosyl, or 2-O -alpha-D-mannopyranosyl-alpha-D-mannopyranosyl; and Y represents hydrogen or a protecting group of the amino function;

and the acid addition salts thereof.

In particular, a group of preferred compounds of this invention comprises those compounds of formula (Ia) wherein R represents:

i) a hydrocarbon radical of formula (a) wherein $R_1$ represents hydrogen, methyl or ethyl, $R_2$, $R_3$ and $R_4$ represents hydrogen, $R_5$ represents methyl or ethyl a hydrocarbon radical of formula (b) wherein $R_1$, $R_2$, $R_3$ and $R_4$ represent hydrogen, and $R_5$ represent a lower alkyl of 1 to 4 carbon atoms, a hydrocarbon radical of formula (e) wherein $R_1$, $R_2$, $R_3$ and $R_4$ represent hydrogen, $R_5$ represent lower alkyl of 1 to 4 carbon atoms and both double bonds have (E) trans configuration, a hydrocarbon radical of formula (e) wherein $R_1$, $R_2$, $R_3$ and $R_4$ represent hydrogen, $R_5$ represents methyl or ethyl and the double bonds have 2 cis (Z) and 4 trans (E) configuration, respectively; or ii) a radical of the formula -A-$R_6$ wherein A represents a bond directly connecting the radical $R_6$ with the carbonyl group or a methylene radical and $R_6$ represents a phenyl radical optionally substituted with a phenyl group or with 1 or 2 substituents selected from methyl, ethyl, methoxy and ethoxy, or a naphthyl radical;

the group RAMO-NH— represents the ramoplanin antibiotic core portion of formula (f) above wherein X represents hydrogen, 2-alpha-D-mannopyranosyl or 2-O -alpha-D-mannopyranosyl-alpha-D-mannopyranosyl, preferably, 2-O-alpha-D-mannopyranosyl-alpha-D-mannopyranosyl; and Y represents hydrogen or a protecting group of the amino function, preferably 9-fluorenylmethoxycarbonyl (FMOC) or benzyloxycarbonyl (CBZ);

and the pharmaceutically acceptable acid addition salt thereof.

Most preferred compounds are those compounds of formula (Ia) wherein R represents:.
- a hydrocarbon radical of formula (a) above wherein $R_1$ represent ethyl, $R_2$, $R_3$ and $R_4$ represent hydrogen, $R_5$ represent methyl;
- a hydrocarbon radical of formula (e) above, wherein $R_1$, $R_2$, $R_3$ and $R_4$ represents hydrogen, $R_5$ represents ethyl and the double bonds have 2 cis (Z) and 4 trans (E) configuration, respectively;
- a hydrocarbon radical of formula (e) above wherein $R_1$, $R_2$, $R_3$ and $R_4$ represent hydrogen, $R_5$ represents ethyl and both double bonds have trans (E) configuration;
- a hydrocarbon radical of formula (e) above wherein $R_1$, $R_2$, $R_3$ and $R_4$ represent hydrogen, $R_5$ is isopropyl and both double bonds have trans (E) configuration;
- a radical -A-$R_6$ wherein A represents a methylene radical, and $R_6$ represents 2-methylphenyl, 2,6-dimethylphenyl, 2-ethylphenyl or 1-naphthyl; and the group RAMO-NH— represents the antibiotic core portion of formula (f) above wherein X represents, hydrogen, -alpha-D-mannopyranosyl or 2-O-alpha-D-mannopyranosyl-alpha-D-mannopyranosyl, preferably, 2-O-alpha-D-mannopyranosyl-alpha-D-mannopyranosyl; and Y represents hydrogen or a protecting group of the amino function, preferably, FMOC or CBZ;

and the pharmaceutically acceptable acid addition salts thereof.

The process for the preparation of the ramoplanin-like amide derivatives of formula (I) and (Ia) of this invention wherein R has the same meaning as above, comprises a two step procedure. The first step (hereinafter "Step a") consists in the amidation of a member of the ramoplanin family or a mixture thereof, wherein the aliphatic acyl side chain is removed and the amino groups of the two ornitine residue at the position 4 and 10 are suitably protected.

Said de-acylated ramoplanin starting materials are herebelow identified as "4,10-protected RAMO-$NH_2$" and are represented by the following formula (III)

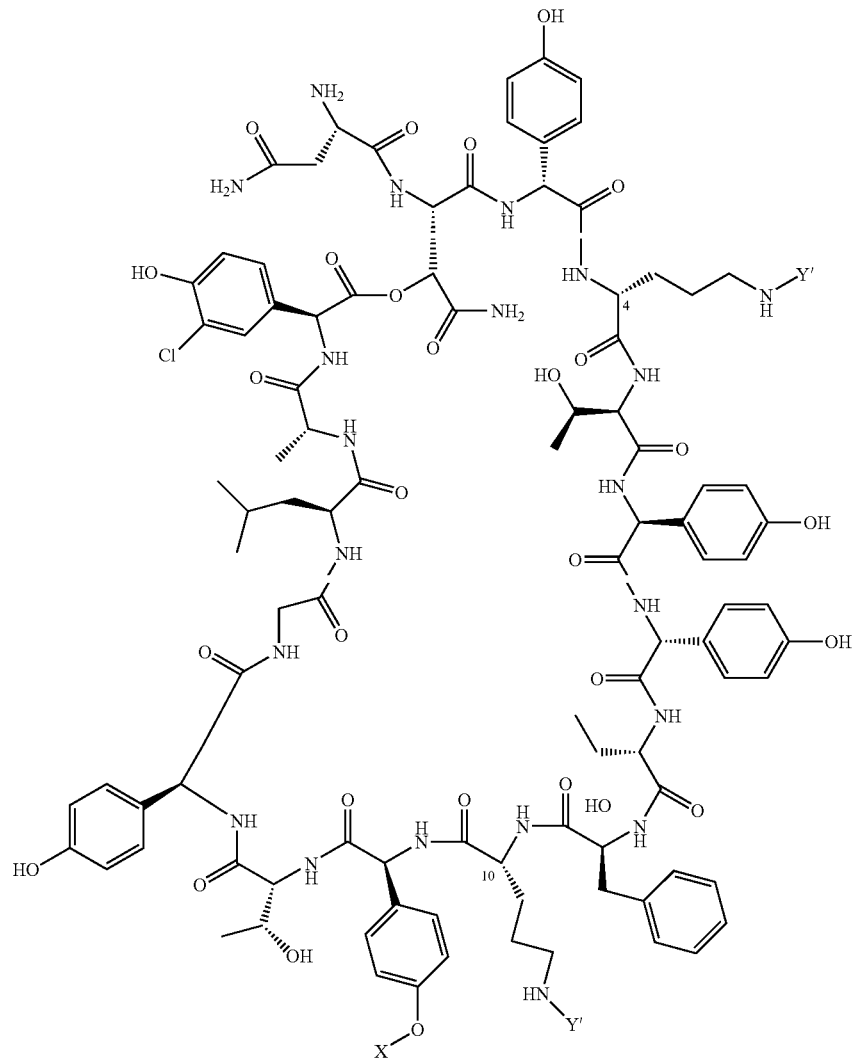

wherein

X represents hydrogen, alpha-D-mannopyranosyl or alpha -D-mannopyranosyl-alpha-D-mannopyranosyl or 2,3-O-di [alpha -D-mannopyranosyl]-alpha-D-mannopyranosyl; and Y' represents a protecting group of the amino function.

The above compounds of formula (III) are novel compounds and, both as the free base form and the acids addition salts thereof, are included within the scope of this application as useful intermediates for preparing the ramoplanin-like amide derivatives of general formula (I) and (Ia).

According to said first step the compounds of formula (I) and (Ia) of this invention are obtained wherein Y represents a protecting group of the amino function.

The second step (hereinafter: Step "b") of the procedure allows the obtainment of the compounds of formula (I) and (Ia) wherein Y is hydrogen. This step consists in the removal of the protecting group from the 4 and 10 ornitine moieties of the compounds obtained through the first amidation step mentioned above. However, as mentioned above, both types of compounds are falling within the scope of the invention. Herebelow a more detailed description of the procedures applied to perform the two steps process is given.

Step a): Amidation

The amidation procedure involves condensing said starting material of formula (III) above, wherein the symbols X and Y' have the same meanings as above with a selected carboxylic acid of formula R—COOH (IV), wherein the symbol R has the same meanings as in formula (I) and (Ia) above, respectively, in the presence of a condensing agent or via formation of an activated ester of said carboxylic acid in the presence of a solvent.

Inert organic aprotic solvents useful for the condensation reaction are those solvents which do not unfavorably interfere with the reaction course and are capable of at least partially solubilizing the antibiotic starting material of formula (III).

Examples of said solvents are organic amides, ethers of glycols and polyols, phosphoramide derivatives, sulfoxides. Preferred solvents are: dimethylformamide, dimethoxyethane, hexamethyl phosphoroamide, dimethylsulphoxide, dioxane, N-methylpyrrolidone and mixtures thereof. Preferably, dimethylformamide (DMF) is employed.

The condensing agent in the present method is one suitable for forming amide bonds in organic compounds and, in particular, in peptide synthesis.

Representative examples of condensing agents are diisopropylcarbodiimide (DIC), dicyclohexylcarbodiimide (DCC) without or in the presence of hydroxybenzotriazole (HOBT), N,N,N',N'-tetramethyl-O-(benzotriazol-1-yl)uronium tetrafluoroborate (TBTU), N,N,N'N'-tetramethyl-O-(7-oxabenzotriazol-1-yl)uronium hexafluorophosphate (HATU), benzotriazolyloxy-tris-(dimethylamino)phosphonium hexafluorophosphate (HBTU), benzotriazolyloxy-tris-(pyrrolidino)phosphonium hexafluorophosphate (PyBOP) and ($C_1$–$C_4$)alkyl, phenyl or heterocyclic phosphorazidates such as, diphenyl-phosphorazidate, dimorpholyl-phosphorazidate.

The preferred condensing agent is PyBOP. The condensing agent is generally employed in a slight molar excess, such as from 1.1 to 1.5; preferably the molar excess of condensing agent is about 1.2 times the molar amount of antibiotic starting compound of formula (III).

According to the present method, the carboxylic acid (IV) is normally used in slight molar excess with respect to the compound of formula (III). In general, a 1 to 3 fold molar excess is used, while a 1.2 fold molar excess is preferred.

It is convenient to add a salt-forming base to the reaction mixture, in an at least equimolecular amount, and preferably in about 1.2 fold molar excess with respect to the starting material of formula (III).

Examples of said salt-forming bases are tertiary organic aliphatic or alicyclic amines such as trimethylamine, triethylamine (TEA), N-methylpyrrolidine or heterocyclic bases such as picoline, and the like, alkali metals (e.g. sodium and potassium) hydrogen carbonates and carbonates.

The reaction temperature will vary considerably depending on the specific starting materials and reaction conditions. In general, it is preferred to conduct the amidation reaction at temperature from 0° C. to 50° C., preferably at room temperature.

Also the reaction time varies considerably, depending on the other reaction parameters; in general the condensation is completed in about 2–24 h.

Generally, the reaction course is monitored by HPLC according to methods known in the art. On the basis of the results of this assays a man skilled in the art will be able to evaluate the reaction course and decide when to stop the reaction and start working up the reaction mass according to known per se techniques which include, for instance, precipitation by addition of non-solvents, extraction with solvents, in conjunction with further common separation operations and purification, e.g. by column chromatography.

The amidation step can also be obtained by reacting the said protected starting materials of formula (III) with the activated ester of the carboxylic acid of formula (IV). The term "activated ester" means an ester which renders the carboxyl function of the acylating group reactive to coupling with the amino group of the protected starting material of formula (III). In such case, the reaction for the formation of the amide is carried out in a polar organic solvent, such as dimethylformamide, at a temperature of about 0° C. to about 50° C., preferably at room temperature, for about 2 to 4 hours.

The activated ester is prepared by esterifying the free acid of the desired acyl group with activating groups such as 4-nitrophenol, 2,4-dinitrophenol, 2,4,5-trichlorophenol, 2-chloro-4,6-dimethoxytriazine, 1-hydroxybenzotriazole, pentafluorophenol, 1-hydroxy-6-chloro-1H-benzotriazole. The preferred activated ester derivative is the ester of the acid R—COOH (IV) with pentafluorophenol or 2,4,5 trichlorophenol.

The carboxylic acids of formula (IV) used as starting materials for the acylation reaction, and their activated derivatives are either known compounds or they can be prepared from known compounds by methods known in the art. According to a preferred method, the activated esters are conveniently prepared by treating the acid chloride of the selected acid of formula (IV) with pentafluorophenol in the presence of a solvent like DMF or by treating the free acid with 2,4,5-trichlorophenol in the presence of 1,3-dicyclohexylcarbodiimide used as a coupling agent or, preferably, by treating the free acid (IV) with pentafluorophenol trifluoroacetate in the presence of pyridine. The pentafluorophenyl or trichlorophenyl ester derivatives, if necessary, may be purified, for example, by column chromatography over silica gel in toluene, methylene chloride, ethyl acetate-hexane.

Step b) Removal of the Protecting Groups

The procedures followed for the removal of the protecting groups from the amidated product depend on the type of the protecting groups utilized.

The protecting groups which are most suitable for protecting the ornitine moieties of the compound of formula (III) above are those protecting groups which can be removed under conditions that are not affecting the stability of the RAMO-NH— portion of the derivatives of formula (I) and (Ia), respectively, and that are compatible with the further reaction steps conditions, in particular, the acidic conditions required for the degradation of the ramoplanin side chain represented by the symbol R' in formula (II) above. Accordingly, said protecting groups are selected from those groups which can be removed by mild base catalyzed solvolysis, hydrogenolysis or reductive cleavage. The most appropriate methods of protection of the amino groups of the 4,10 ornitine moieties may be selected by the skilled technician also by relying on the indications given in the commonly known text books dealing with protection of amino group in peptide synthesis. For instance, when the amino groups are protected by way of formation of a carbamate with a benzyloxycarbonyl group, catalytic hydrogenation may represent the most preferred procedure for the removal of the protecting groups. The hydrogenation is usually carried out at room temperature at a pressure which corresponds to the atmospheric pressure or of 1–2 atmospheres over the atmospheric pressure, in the presence of an hydrogenation catalyst, e.g. 5% to 10% Pd/BaSO$_4$ or 5% Pd/C, in an inert organic solvent such as lower alkanols, dimethylformamide, dioxane, tetrahydrofuran and their mixtures, and an acid, for example, glacial acetic acid or a diluted aqueous mineral acid, e.g. 0.1N hydrochloric acid.

A one pot procedure can be utilized when the removal of the protecting groups of the ornitine moieties can be obtained by addition of a amine. For instance, when the starting material of formula (III) is protected with a 9-fluorenylmethoxycarbonyl (FMOC) group or similar protecting groups, the deprotection step can be carried on directly on the condensation reaction mixture without working up the condensation reaction mass. In this case a 1–50% (volume/volume) of a suitable amine is added to the reaction solution. Examples of amines that can be added to the solution containing the protected product of formula (I) and (Ia), respectively, are triethylamine, N-methylpyrroline, piperidine, 2,2,6,6-tetramethylpiperidine, and N-methylpiperazine.

The reaction time will vary considerably, depending on the amine utilized and the other reaction parameters, such as temperature and solvent. In general, this step is completed in a period of time of few minutes to about 24 hours. In any case, the reaction course is monitored by HPLC according to the methods known in the art. On the basis of the results of these assays, a man skilled in the art will be able to evaluate the reaction course and decide when to stop the reaction and start working-up the reaction mass according to per se known techniques which include, for instance, extraction with solvents, precipitation by addition of non-solvents, in conjunction with further common separation operations and purification, e.g. by column chromatography.

The compound of formula (I) and (Ia) wherein the symbol Y in the group RAMO-NH— of formula (f) represents hydrogen and the symbol X represents alpha-D-mannopyranosyl, 2-O -alpha-D-mannopyranosyl-alpha-D-mannopyranosyl or 2,3-O -di[alpha-D-mannopyranosyl]-alpha-D-mannopyranosyl can be transformed into the corresponding compounds of formula (I) and (Ia) wherein X represent hydrogen by means of the method described for the preparation of the aglycones of ramoplanin in EP-B-0337203. This procedure represents an alternative method with respect to the direct amidation of a compound of formula (III) wherein X represents hydrogen.

Method for Obtaining the Suitably Protected Starting Material of Formula (III).

The suitably protected starting material of formula (III), can be obtained by a chemical degradation in four steps of the unsaturated aliphatic acyl side chain of a compound of the ramoplanin antibiotics of formula (II) above, wherein R' and R" have the above meanings, or any mixture thereof, including the ramoplanin complex as currently obtained in the practice.

The degradation sequence is formed by a first protection of the 4,10-ornitine moieties of a compound of the ramoplanin family of formula (II) or a mixture thereof followed by a reductive ozonolysis. The resulting aldehyde, "4,10-protected RAMO-NH—CO—CHO", is aminated with a primary amine in the presence of a reducing agent and the resulting amino acyl compound "4,10-protected RAMO-NH—CO—CH$_2$—NH—R$_7$", wherein R$_7$ represents the hydrocarbon portion of the primary amine, is subjected to Edman degradation to obtain the deacyl ramoplanin compound (III) suitably protected on the ornitine moieties ("4, 10-protected RAMO-NH$_2$").

Step 1: Protection of the Amine Moieties of Compounds of Formula (II)

Any typical protecting group of the amino rest, which is resistant to the conditions applied during the process of this invention and may be readily removed under conditions which do not effect the stability of the ramoplanin core portion can be utilized here. Suitable protecting groups of the amino function can be selected, for instance, from the groups described in: T. W. Greene, "Protective Groups in Organic Synthesis", J. Wiley, N. Y., 1981.

In particular, in this case, those protecting groups, which are formed by acylating the amino moiety, are preferred. The protecting groups employed in the process herein described are those generally employed in peptides synthesis. Preferably, the N-protection of the ornitine moieties is performed with protecting groups that are easily removable under mild basic conditions or through catalitic hydrogenation such as 9-fluorenylmethoxycarbonyl (FMOC), 9-(2-sulfo)fluorenylmethoxycarbonyl, 9-(2,7-dibromo)fluorenylmethoxycarbonyl, 2-chloro-3-indenylmethoxycarbonyl, benz(f)inden-3-ylmethoxycarbonyl, 2,7-di-t-butyl-[9-(10,10dioxo-10,10, 10,10-tetrahydrothioxanthyl)]methoxycarbonyl 1,1-dimethyl-2-cyanoethoxycarbonyl, allyloxycarbonyl, cinnamyloxycarbonyl, N-hydroxypiperidinyloxycarbonyl, benzyloxycarbonyl (CBZ), p-nitrobenzyloxycarbonyl, 3,4-dimethoxy-6-nitrobenzyloxycarbonyl, 2,4-dichlorobenzyloxycarbonyl, 9-anthrylmethyloxycarbonyl and diphenylmethoxycarbonyl. Usually, said acylating agents are those reactants providing an alkanoyl or aroyl group, or a carbonate moiety such as the acids halides, anhydrides, or activated esters.

Use of protecting groups which are removable only through catalytic hydrogenation is, however, avoided when a compound of formula (I) and (Ia) above is desired wherein the radical R contains an aliphatic double bonds moiety which may be sensitive to the hydrogenation conditions.

According to a preferred embodiment of the invention, the amino groups are protected in a first stage by introduction of a lower alkoxycarbonyl or an aryl-lower alkoxycarbonyl radical, for instance, a fluorenylmethoxycarbonyl radical. For this purpose, the starting compound of the ramoplanin family of formula (II) or a mixture thereof is reacted with a reagent capable of inserting said radical onto the amino group such as, benzyl chloroformate, dibenzylcarbonate, N-(9-fluorenylmethoxycarbonyloxy)succinimide, in the presence of an excess of a mild base. The most preferred protecting group of the ornitine moieties is FMOC. The reaction is usually carried out in the presence of a solvent at a temperature between 0 and 50° C., preferably between 15 and 25° C. Usually, the reagent providing the protecting group is employed in about equimolecular amount or in a slight excess with respect to the number of the amino groups of the ramoplanin family starting material (II) requiring protection. In the usual cases, since the amino groups of the starting material of the ramoplanin family of formula (II) requiring protection are those of the two ornithine moieties in the positions 4 and 10, about two equimolecular amounts of protecting agent for each equimolecular amount of the starting material (II) are employed. The solvent is usually selected from acetone, tetrahydrofuran, dioxane, dimethylsulfoxide, dimethylformamide and mixtures thereof or mixtures of any of said solvents with water.

The mild bases, which are preferably utilized, are selected from alkali metal carbonates, alkali metal bicarbonates (e.g. potassium carbonate and sodium bicarbonate), tri-(lower alkyl) amines (e.g. triethylamine), and mixtures thereof.

Step 2: Reductive Ozonolysis

The reaction involves treating the starting material of formula (II), suitably protected on the ornitine moieties according to Step 1 above, with ozone.

Inert organic solvents useful for the reductive ozonolysis reaction are those solvents that do not unfavorably interfere with the reaction course and are capable of at least partially solubilizing the antibiotic starting material.

Examples of said solvents are organic amides, halogenated lower aliphatic hydrocarbon, ethers of glycols and polyols, alcohols, phosphoramide derivatives, sulfoxides. Preferred solvents are: dimethylformamide, methanol, dichloromethane, dichloroethane, dimethoxyethane, hexamethylphosphoroamide, dimethylsulphoxide, dioxane and mixtures thereof. Most preferably a mixture of methanol: dimethylformamide is employed.

According to the present method, ozone is normally bubbled into the solution in a molar excess. In general, 2 to 8 fold molar excess is used, while a 4 fold molar excess is preferred.

The reaction temperature will vary considerably, depending on the specific starting materials and reaction conditions. In general, it is preferred to conduct the reaction at temperature from −90° C. to −20° C., preferably at −78° C.

Also the reaction time varies considerably depending on the other reaction parameters; in general, the ozonolysis is completed in about 5 minutes to 2 hours.

Conversion of the obtained ozonides to the corresponding aldheydes can be achieved with a suitable reducing agent. Examples of these reducing agents are dimethyl sulfide, bisulfite, triphenylphosphine, thiourea and hydrogen in the presence of a hydrogenation catalyst; preferably triphenylphosphine is used.

Generally, the reaction course is monitored by HPLC according to methods known in the art. On the basis of the results of this assays a man skilled in the art will be able to evaluate the reaction course and decide when to stop the reaction and start working up the reaction mass according to per se known techniques which include, for instance, precipitation by addition of non-solvents, extraction with solvents, in conjunction with further common separation operations and purification, e.g. by column chromatography.

The product resulting from this Step 2 corresponds to the ramoplanin starting material of formula (II), protected on the two amino group of the 4,10-ornitine moieties wherein the unsaturated acyl chain represented by R' is replaced by a group —CO—CHO (4,10-protected RAMO-NHCOCHO).

Step 3: Reductive Amination

The reductive amination procedure involves condensing the aldehyde obtained according to Step 2, with the appropriate primary amine in the presence of a reducing agent.

Examples of said primary amines are $C_1$–$C_4$ lower alkylamines, benzylamine.

Preferably benzylamine is employed.

Inert organic solvents useful for the reductive amination reaction are those solvents which do not unfavorably interfere with the reaction course and are capable of at least partially solubilizing the aldehyde.

Examples of said solvents are alkanols, organic amides, ethers of glycols and polyols, phosphoramide derivatives, and sulfoxides. Preferred solvents are: dimethylformamide, methanol, dimethoxyethane, hexamethylphosphoroamide, dimethylsulphoxide, dioxane and mixtures thereof. Preferably dimethylformamide (DMF) is employed.

According to the present method, the amine is normally used in a molar excess. In general, a 1 to 7 fold molar excess is used, while a 5 fold molar excess is preferred.

The amine reactant is preferably used in salified form, most preferably as salt with a strong acid, particularly preferred being the hydrohalic acids, the most preferred being hydrobromic acid and hydrochloric acid.

The reaction temperature will vary considerably depending on the specific starting materials and reaction conditions. In general, it is preferred to conduct the reaction at temperature from 0° C. to 50° C., preferably at room temperature.

Also the reaction time varies considerably depending on the other reaction parameters; in general the condensation is completed in about 2–24 hours.

The reducing agents in the present method are those suitably employed for reducing imine bonds in organic compounds. Representative examples of such reducing agents are sodium cyanoborohydride, sodium borohydride, triethoxyborohydride. The preferred reducing agent is sodium cyanoborohydride. The reducing agent is generally employed in a slight molar excess, such as from 1.1 to 1.8 molar excess; preferably, the molar excess of reducing agent is 1.5 times the amount of the aldehyde compound.

Generally, the reaction course is monitored by HPLC according to methods known in the art. On the basis of the results of this assays a man skilled in the art will be able to evaluate the reaction course and decide when to stop the reaction and start working up the reaction mass according to per se known techniques which include, for instance, extraction with solvents, precipitation by addition of non-solvents, in conjunction with further common separation operations and purification, e.g. by column chromatography.

The amines used in the above condensation are either commercially available compounds or are prepared according to per se known techniques.

The product resulting from this Step 3 corresponds to the ramoplanin starting material of formula (II) wherein the unsaturated acyl chain represented by R' is replaced by a group —CO—$CH_2$—$NHR_7$ wherein $R_7$ represents the hydrocarbon portion of the primary amine reactant (4,10-protected RAMO-NH—$COCH_2NHR_7$).

Step 4: Edman Degradation

The Edman degradation and its successive evolutions are methods currently applied in the peptide chemistry to remove the N-terminal amino acids from the peptidic chain (see: "The Merck Index", 13th Ed, ONR-29, Merck & Co Inc., 2001, and the references cited therein).

According to the more recent developments of the original procedure, the Edman degradation essentially consists in reacting a peptide containing terminal amino group residue(s) with a lower alkyl or aryl isothiocyanate (e.g. methylisothiocyanate, phenylisothiocyanate, p-nitrophenylisothiocyanate and naphthyliso-thiocyanate) to form a thiocarbamyl-peptide derivative which is then submitted to cleavage of the terminal thiocarbamyl amino acid portion by cyclization to thiohydantoin derivative.

This last step results in the selective elimination of the N-terminal amino acid(s) of the peptidic chain.

According to a preferred embodiment of this step, the Edman degradation is carried out on the N-terminal amino acid of the compound obtained from the reductive amination of Step 3, by reacting the above mentioned starting material with a 0.2–0.5 molar excess of methylisothiocyanate or phenylisothiocyanate, over the stoichiometric amount at a pH value between 8 and 9 in an aqueous solvent mixture (e.g. pyridine:water 1:1) at a temperature between 0 and 35° C., preferably at room temperature. The obtained methyl (or phenyl) thiocarbamyl intermediate may be isolated from the reaction mixture according to common procedures and then submitted to cleavage/cyclization without any further purification.

The cleavage/cyclization procedure involves heating the above intermediate in an acidic medium which does not affect the other essential portions of the molecule. For instance, this step may be suitably performed by dissolving the thiocarbonyl intermediate into trifluoroacetic acid (TFA) and maintaining this solution at 40–60° C. for a period of time which is sufficient to complete the reaction (HPLC control may be applied).

In most cases, heating may not be necessary and the cleavage/cyclization reaction occurs even at temperature comprised between 10 and 40° C.

The resulting reaction mixture is evaporated to dryness and then washed with a solvent which is capable of removing the thiohydantoin side product, or it is purified by method per se known in the art, e.g. by reverse-phase column chromatography. The obtained 4,10-protected RAMO-$NH_2$ derivative of formula (III) above is a key intermediate for the amidation and de-protection steps described above to yield the products of formula (I) and (Ia) of this invention.

As specified above, the process for the preparation of the compound of formula (I) herein described includes also the preparation of each single factor $A_1$, $A_2$, $A_3$, $A'_1$, $A'_2$ and $A'_3$ of ramoplanin and of ramoplanose represented in the formula (II) above wherein R' and R" have the same meaning as specified above, as well as their corresponding tetrahydroderivative derivatives and aglycones.

The possibility of synthesizing each single component of the ramoplanin complex, not accompanied by the other components which are always present in the natural product, is a valid alternative to the laborious separation procedure of the single components from the complex described in U.S. Pat. No. 4,427,656 and EP 318680, when, for any particular reason obtaining large amounts of a single unitary product is desirable.

When at least one of the symbols Y represent hydrogen, the compounds of formula (I) and (Ia) of the invention can form acid addition salts according to conventional procedures.

Preferred addition salts of the compounds of this invention are the "pharmaceutically acceptable acid addition salts" which are intended as those salts with acids which from biological, manufacturing and formulation standpoint are compatible with the pharmaceutical practice as well as with the use in the animal growth promotion.

Representative and suitable acid addition salts of the compounds (I) and (Ia) include those salts formed by standard reaction with both organic and inorganic acids such as, for example, hydrochloric, hydrobromic, sulfuric, nitric, phosphoric, acetic, trifluoroacetic, trichloroacetic, succinic, citric, ascorbic, lactic, maleic, fumaric, palmitic, cholic, pamoic, mucic, glutamic, camphoric, glutaric, glycolic, phtalic, tartaric, lauric, stearic, salicylic, methanesulfonic, dodecylsulfonic (estolic), benzenesulfonic, sorbic, picric, benzoic, cinnamic acid and the like.

The transformation of the free amino or non-salts compounds of the invention into the corresponding addition salts, and the reverse, i.e. the transformation of an addition salts of a compound of the invention into the non-salt or free amino form, are within the ordinary technical skill and are encompassed by the present invention. The only precaution is to avoid solutions with pH higher than 8–9 when freeing the base (for avoiding the opening of the lactonic moiety). For instance, a free amino compound of formula (I) and (Ia) can be transformed into the corresponding acid addition-salt by dissolving the non-salt form in an aqueous solvent and adding a slight molar excess of the selected acid. The resulting solution or suspension is then lyophilized to recover the desired salt. Instead of lyophilizing, in some instances, it is possible to recover the final salt by extraction from an aqueous solution thereof with a water immiscible organic solvent wherein the salt form is soluble, concentration to a small volume of the separated organic phase and precipitation by adding a non-solvent.

In case the final salt is insoluble in an organic solvent where the non-salt form is soluble, it may be recovered by filtration from the organic solution of the non-salt form after addition of the stoichiometric amount or a slight excess of the selected acid.

The non-salt form can be prepared from a corresponding acid salt dissolved in an aqueous solvent, which is then neutralized to free the non-salt form. This latter is recovered, for instance, by extraction with a water immiscible organic solvent or is transformed into another acid addition salt by adding the selected acid and working up as above.

A common desalting procedure may be employed when, following the neutralization, desalting is necessary.

For example, column chromatography on controlled pore polydextrane resins (such as Sephadex LH 20) or silanized silica gel may be conveniently used. After eluting the undesired salts with an aqueous solution, the desired product is eluted by means of linear gradient or step-gradient of a mixture of water and a polar or apolar organic solvent.

As known in the art, the salt formation either with pharmaceutically acceptable acids or non-pharmaceutically acceptable acids may be used as a convenient purification technique. After formation and isolation, the salt form of a compound of formula (I) and (Ia) can be transformed into the corresponding non-salt or into a pharmaceutically acceptable salt.

In some instances the acid addition salt of a compound of formula (I) and (Ia) is more soluble in water and hydrophilic solvents and has an increased chemical stability. Good solubility and stability in water or hydrophilic solvents of an active compound are in general appreciated in the art, for the preparation of suitable pharmaceutical compositions for the administration of the medicament.

However, in view of the similarity of the properties of the compounds of formula (I) and (Ia) with their salts, what is said in the present application when dealing with the biological activities of the non-salt compounds of formula (I) and (Ia) applies also to their pharmaceutically acceptable salts, and vice versa.

The following TABLE 1 shows a series of compounds which can be prepared according to the general method of this invention.

TABLE 1

| Compound N° | R | X[1] | Y |
|---|---|---|---|
| 1 | 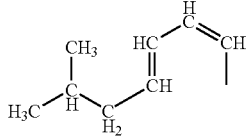 | MM | H |
| 2 | 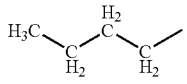 | MM | H |
| 3 | 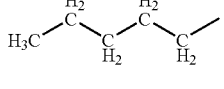 | MM | H |
| 4 | 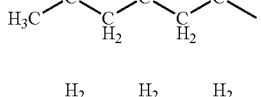 | MM | H |
| 5 | 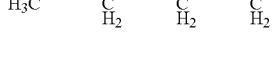 | MM | H |
| 6 | 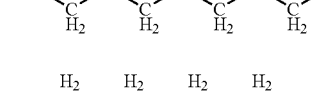 | MM | H |
| 7 | 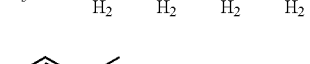 | MM | H |
| 8 |  | MM | H |
| 9 | 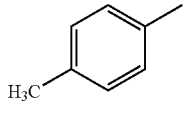 | MM | H |
| 10 | 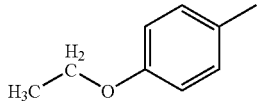 | MM | H |
| 11 | 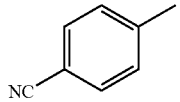 | MM | H |

TABLE 1-continued

| Compound N° | R | X[1] | Y |
|---|---|---|---|
| 12 | 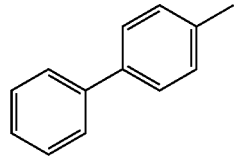 | MM | H |
| 13 | 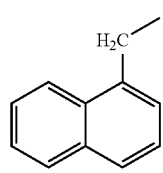 | MM | H |
| 14 | 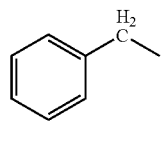 | MM | H |
| 15 | 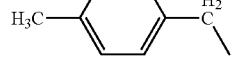 | MM | H |
| 16 |  | MM | H |
| 17 | 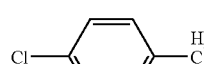 | MM | H |
| 18 |  | MM | H |
| 19 | 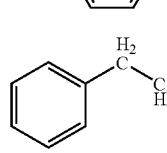 | MM | H |
| 20 | 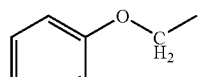 | MM | H |
| 21 | 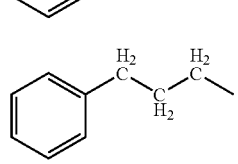 | MM | H |
| 22 | 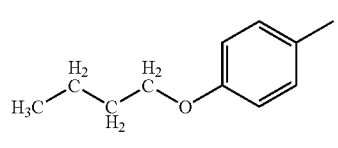 | MM | H |
| 23 | 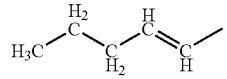 | MM | H |

TABLE 1-continued

RAMO—NH—CO—R [formula (1)]

| Compound N° | R | X¹⁾ | Y |
|---|---|---|---|
| 24 | H₃C—CH₂—CH₂—CH₂—CH₂—CH=CH—CH₃ | MM | H |
| 25 | H₃C—CH=CH—CH=CH—CH₃ | MM | H |
| 26 | 3-methylphenyl | MM | H |
| 27 | 1-naphthyl | MM | H |
| 28 | 2-naphthyl | MM | H |
| 29 | 2-naphthylmethyl | MM | H |
| 30 | 4-biphenylmethyl | MM | H |
| 31 | | MM | H |
| 32 | | MM | H |
| 33 | | MM | H |
| 34 | | MM | H |
| 35 | | MM | H |
| 36 | | MM | H |
| 37 | H₃C—CH₂—CH=CH—CH=CH—CH₃ | MM | H |
| 38 | | MM | H |
| 39 | | MM | H |
| 40 | | MM | H |
| 41 | | H | H |
| 42 | | H | H |
| 43 | | H | H |
| 44 | | H | H |
| 45 | | MMM | H |
| 46 | | MMM | H |
| 47 | 2-methyl-isopropylphenyl | MM | H |
| 48 | | MM | H |
| 49 | | MM | H |
| 50 | | MM | H |
| 51 | | MM | H |
| 52 | | MM | H |
| 53 | | MM | H |
| 54 | | MM | H |
| 55 | | MM | H |
| 56 | | MM | H |
| 57 | | MM | H |
| 58 | | MM | H |
| 59 | H₃C—CH₂—O—CH₂—CH₂—CH₂—CH₃ | MM | H |
| 60 | CF₃—CH₂—O—CH₂—CH₂—CH₂—CH₃ | MM | H |
| 61 | 2,3-dimethylnaphthyl | MM | H |
| 62 | | MM | H |
| 63 | 2-ethyl-3-methylpentyl | MM | H |
| 64 | | MM | H |
| 65 | | MM | H |
| 66 | | MM | H |
| 67 | | MM | H |
| 68 | | MM | H |
| 69 | | MM | H |

TABLE 1-continued
RAMO—NH—CO—R [formula (1)]
| Compound N° | R | X[1] | Y |
|---|---|---|---|
| 70 | | MM | H |
| 71 | | MM | H |
| 72 | | MM | H |
| 73 | | MM | H |
| 74 | | MM | H |
| 75 | | MM | H |
| 76 | | MM | H |
| 77 | | MM | H |
| 78 | | MM | H |
| 79 | | MM | H |
| 80 | | MM | H |
| 81 | | MM | H |
| 82 | | MM | H |
| 83 | | MM | H |
| 84 | | MM | H |
| 85 | | MM | H |
| 86 | | MM | H |
| 87 | | MM | H |
| 88 | | MM | H |
| 89 | | MM | H |
| 90 | | MM | H |
| 91 | 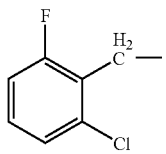 | MM | H |
| 92 | 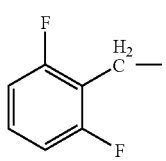 | MM | H |
| 93 | 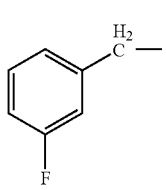 | MM | H |
| 94 | 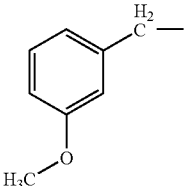 | MM | H |
| 95 | 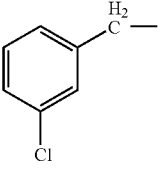 | MM | H |
| 96 | 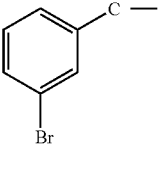 | MM | H |
| 97 | 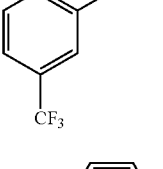 | MM | H |
| 98 | 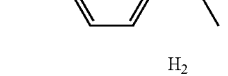 | MM | H |
| 99 | 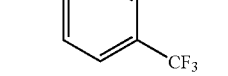 | MM | H |
| 100 | 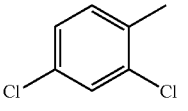 | MM | H |
| 101 | 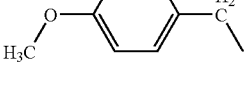 | MM | H |
| 102 | 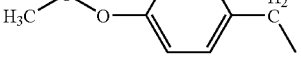 | MM | H |
| 103 | 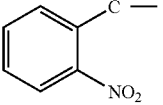 | MM | H |

TABLE 1-continued

RAMO—NH—CO—R [formula (1)]

| Compound N° | R | X[1)] | Y |
|---|---|---|---|
| 104 | 4-O₂N-C₆H₄-CH₂- | MM | H |
| 105 | 2-(CH₃S)-C₆H₄- | MM | H |
| 106 | 4-(CH₃S)-C₆H₄-CH₂- | MM | H |
| 107 | 2,5-(CH₃)₂-C₆H₃-CH₂- | MM | H |
| 108 | 3,5-(CH₃)₂-C₆H₃-CH₂- | MM | H |
| 109 | 2,4-(CH₃O)₂-C₆H₃-CH₂- | MM | H |
| 110 | 3,4-(CH₃O)₂-C₆H₃-CH₂- | MM | H |
| 111 | 2,3-F₂-C₆H₃-CH₂- | MM | H |
| 112 | 3,4-F₂-C₆H₃-CH₂- | MM | H |
| 113 | 2,5-F₂-C₆H₃-CH₂- | MM | H |
| 114 | 3,5-F₂-C₆H₃-CH₂- | MM | H |
| 115 | 2-Cl-4-F-C₆H₃-CH₂- | MM | H |
| 116 | 2,6-F₂-C₆H₃-CH₂- | MM | H |
| 117 | (R)-C₆H₅-CH(CH₃)- | MM | H |
| 118 | (S)-C₆H₅-CH(CH₃)- | MM | H |
| 119 | CH₃-CH₂-C(CH₂CH₃)=CH-CH₃ | MM | H |
| 120 | CH₃-CH₂-C(CH₂CH₃)=C(CH₃)-CH₃ | MM | H |
| 121 | CH₃-CH₂-CH(CH₂CH₃)-CH=CH-CH₃ | MM | H |
| 122 | CH₃-CH₂-CH(CH₂CH₃)-CH₂-CH₂-CH₃ | MM | H |

TABLE 1-continued

RAMO—NH—CO—R [formula (1)]

| Compound N° | R | X[1] | Y |
|---|---|---|---|
| 123 | (isohexyl branched alkyl) | MM | H |
| 124 | (branched alkyl) | MM | H |
| 125 | (branched alkyl) | MM | H |
| 126 | (branched alkyl) | MM | H |
| 127 | (branched alkyl) | MM | H |
| 128 | 2-(trifluoromethylthio)benzyl | MM | H |
| 129 | 4-(trifluoromethylthio)benzyl | MM | H |
| 130 | (4-fluorophenoxy)methyl | MM | H |
| 131 | (2-nitrophenoxy)methyl | MM | H |
| 132 | 2-cyanobenzyl | MM | H |
| 133 | (2,4,6-trifluorophenoxy)methyl | MM | H |

As it can be observed from the above TABLE 1, compound 1, 5 and 35 which are falling within formula (I) above, but not in formula (Ia), are known compounds in that they correspond to ramoplanin factor $A_2$, the tetrahydro-derivative of ramoplanin factor $A_1$ and ramoplanin factor $A_1$, respectively.

The antimicrobial activity in vitro of the compounds obtained according to the process of this invention was evaluated against a panel of clinical isolates of methicillin-sensitive, methicillin-resistant and vancomycin-intermedie *Staphylococcus aureus*, Van-S and Van-A *Enterococcus faecium* and *faecalis, Streptococcus pyogenes, Escherichiae coli* and *Candida albicans*.

MICs were performed using the broth microdilution methodology following the NCCLS procedure (NCCLS Document M7-A4 Vol.17 No.2 January 1997) in presence of 0.02% albumine bovine serum with inocula of approximately $5 \times 10^5$ cfu/mL. The media employed included cation-adjusted Mueller-Hinton (MH) broth (Difco Laboratories, Detroit, Mich., USA) supplemented or not with 30% (v/v) bovine serum. Tests were read after 24 h incubation at 37° C.

In the following TABLE 2 are reported the MIC (Minimum Inhibitory Concentration) values of some representative compounds identified in the above TABLE 1.

TABLE 2

Microbiological activity (isolated compounds) MIC mcg/ml

| MICROORGANISM | COMPOUND N° | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| 819 Staph. aureus Smith | 0.125 | 8 | 4 | 0.125 | 0.25 | 0.25 | 2 | 8 | 4 | 1 | 8 | 0.06 | 0.06 | 1 | ≦0.125 |
| +30% bovine serum | 4 | 8 | 4 | 1 | 4 | 8 | 32 | 4 | 2 | 1 | 4 | 2 | 0.25 | 1 | 0.5 |
| 613 Staph. aureus clin. isolate Met-R | 0.25 | 8 | 4 | 0.25 | 0.5 | 1 | 2 | 4 | 4 | 1 | 4 | 0.13 | 0.13 | 1 | ≦0.125 |
| 3797 Staph. aureus clin. isolate VISA Met-R | 2 | >32 | 32 | 2 | 4 | 8 | 8 | >32 | 4 | 4 | 32 | 1 | 0.25 | 4 | 4 |
| 3798 Staph. aureus clin. isolate VISA | 1 | 32 | 16 | 1 | 2 | 4 | 4 | 32 | 8 | 2 | 32 | 0.25 | 0.25 | 2 | 2 |
| +30% bovine serum | 16 | n.a.* | n.a.* | 2 | n.a.* | n.a.* | n.a.* | n.a.* | n.a.* | 2 | n.a.* | 16 | 2 | 2 | 4 |
| 49 Strep. pyogenes C203 | <0.03 | 0.125 | 0.125 | ≦0.06 | <0.03 | 0.125 | 0.25 | 0.125 | <0.03 | ≦0.06 | 0.06 | <0.03 | <0.03 | ≦0.06 | ≦0.125 |
| 559 Entero. faecalis (isogenic of L 560) | 0.06 | 8 | 2 | 0.25 | 0.125 | 0.06 | 0.125 | 4 | 2 | 1 | 4 | 0.06 | 0.06 | 2 | 0.25 |
| 560 Entero. faecalis VanA | 0.06 | 8 | 2 | 0.25 | 0.06 | 0.06 | 0.06 | 4 | 2 | 1 | 8 | <0.03 | <0.03 | 2 | ≦0.125 |
| +30% bovine serum | 2 | 8 | 4 | 0.25 | 2 | 4 | 8 | 8 | 4 | 1 | 16 | 2 | 0.5 | 2 | 1 |
| 568 Entero. faecium (isogenic of L569) | 0.125 | 8 | 4 | 0.25 | 0.25 | 0.125 | 0.25 | 8 | 4 | 2 | 8 | <0.03 | <0.03 | 2 | 0.5 |
| 569 Entero. faecium clin. isolate Van-A | 0.125 | 8 | 4 | 0.125 | 0.125 | <0.03 | 0.06 | 4 | 2 | 1 | 8 | <0.03 | <0.03 | 1 | 0.5 |
| +30% bovine serum | 2 | 8 | 8 | 1 | 4 | 4 | 8 | 8 | 2 | 2 | 8 | 2 | 1 | 1 | 2 |
| 47 E coli SKF12140 | >32 | >32 | >32 | >64 | >32 | >32 | >32 | >32 | >32 | >64 | >32 | >128 | >128 | >64 | >128 |
| 145 Candida albicans SKF2270 | >32 | >32 | >32 | >64 | >32 | >32 | >32 | >32 | >32 | >64 | >32 | >128 | >128 | >64 | >128 |

| MICROORGANISM | COMPOUND N° | | | | | | | | | | | | | | |
|---|---|---|---|---|---|---|---|---|---|---|---|---|---|---|---|
| | 16 | 17 | 18 | 19 | 20 | 21 | 22 | 23 | 24 | 25 | 26 | 27 | 28 | 29 | 30 |
| 819 Staph. aureus Smith | 2 | 0.5 | 0.5 | 16 | 4 | 1 | 0.25 | 1 | 0.125 | 2 | 4 | 1 | 0.125 | 0.25 | 0.13 |
| +30% bovine serum | 2 | 2 | 2 | 4 | 4 | 4 | 4 | 1 | 1 | 4 | 8 | 8 | 4 | 2 | 4 |
| 613 Staph. aureus clin. isolate Met-R | 2 | 0.5 | 0.5 | 2 | 8 | 2 | 0.5 | 1 | 0.25 | 4 | 4 | 2 | 0.25 | 0.25 | 0.25 |
| 3797 Staph. aureus clin. isolate VISA Met-R | 8 | 4 | 4 | 8 | 32 | 8 | 4 | 4 | 2 | 16 | 16 | 8 | 2 | 1 | 1 |
| 3798 Staph. aureus clin. isolate VISA | 8 | 2 | 2 | 8 | 16 | 8 | 4 | 2 | 1 | 8 | 8 | 8 | 1 | 1 | 1 |
| +30% bovine serum | 8 | 8 | 8 | 16 | 16 | 16 | 32 | 2 | 2 | 16 | 16 | 16 | 16 | 8 | 16 |
| 49 Strep. pyogenes C203 | 0.06 | <0.03 | <0.03 | <0.03 | 0.06 | <0.03 | 0.125 | ≦0.06 | ≦0.06 | 0.125 | 0.06 | ≦0.03 | ≦0.03 | ≦0.03 | ≦0.03 |
| 559 Entero. faecalis (isogenic of L 560) | 2 | 0.5 | 0.5 | 2 | 8 | 4 | 0.25 | 2 | 0.25 | 2 | 2 | 0.5 | 0.125 | 0.125 | 0.06 |
| 560 Entero. faecalis VanA | 2 | 0.5 | 0.5 | 2 | 4 | 1 | 0.25 | 2 | 0.125 | 2 | 4 | 0.5 | 0.25 | 0.125 | 0.06 |
| +30% bovine serum | 4 | 4 | 2 | 4 | 8 | 4 | 8 | 2 | 0.25 | 4 | 8 | 4 | 4 | 2 | 4 |
| 568 Entero. faecium (isogenic of L569) | 4 | 1 | 1 | 1 | 4 | 2 | 0.25 | 2 | 0.25 | 2 | 4 | 1 | 0.25 | 0.25 | 0.13 |
| 569 Entero. faecium clin. isolate Van-A | 4 | 1 | 0.5 | 2 | 16 | 4 | 0.25 | 1 | ≦0.06 | 8 | 4 | 4 | 0.25 | 0.25 | 0.06 |
| +30% bovine serum | 8 | 4 | 4 | 8 | 16 | 4 | 8 | 2 | 1 | 8 | 8 | 8 | 16 | 8 | 16 |
| 47 E coli SKF12140 | >32 | >32 | >32 | >32 | >32 | >32 | >32 | >64 | >64 | >32 | >32 | >32 | 32 | 32 | 32 |
| 145 Candida albicans SKF2270 | >32 | >32 | >32 | >32 | >32 | >32 | >32 | >64 | >64 | >32 | >32 | >32 | >32 | >32 | >32 |

TABLE 2-continued

Microbiological activity (isolated compounds) MIC mcg/ml

| MICROORGANISM | COMPOUND N° | | | | | | | | | |
|---|---|---|---|---|---|---|---|---|---|---|
| | 31 | 32 | 33 | 34 | 35 | 36 | 37 | 38 | 39 | 40 |
| 819 Staph. aureus Smith | 4 | <0.125 | <0.125 | <0.125 | <0.125 | <0.125 | 0.25 | 1 | <0.125 | 0.25 |
| +30% bovine serum | 4 | 0.5 | 1 | 1 | 0.5 | 0.5 | 0.5 | 1 | 0.25 | 0.5 |
| 613 Staph. aureus clin. isolate Met-R | 4 | <0.125 | <0.125 | 0.25 | <0.125 | <0.125 | 0.25 | 1 | <0.125 | 0.25 |
| 3797 Staph. aureus clin. isolate VISA Met-R | 16 | 1 | 1 | 2 | 1 | 1 | 2 | 8 | 2 | 2 |
| 3798 Staph. aureus clin. isolate VISA | 16 | 0.5 | 0.5 | 1 | 0.5 | 0.5 | 1 | 8 | 1 | 1 |
| +30% bovine serum | 16 | 2 | 4 | 4 | 2 | 2 | 2 | 4 | 1 | 2 |
| 49 Strep. pyogenes C203 | 0.13 | <0.125 | <0.125 | <0.125 | <0.125 | <0.125 | <0.125 | £0.125 | <0.125 | <0.125 |
| 559 Entero. faecalis (isogenic of L 560) | 2 | <0.125 | <0.125 | 0.25 | <0.125 | <0.125 | 0.5 | 2 | 0.5 | 0.5 |
| 560 Entero. faecalis VanA | 2 | <0.125 | <0.125 | <0.125 | <0.125 | <0.125 | 0.25 | 2 | 0.25 | 0.25 |
| +30% bovine serum | 4 | 0.5 | 0.5 | 1 | 0.5 | 0.5 | 0.5 | 2 | 0.5 | 1 |
| 568 Entero. faecium (isogenic of L569) | 4 | <0.125 | <0.125 | 0.25 | <0.125 | <0.125 | 0.5 | 2 | 0.5 | 0.5 |
| 569 Entero. faecium clin. isolate Van-A | 4 | <0.125 | <0.125 | <0.125 | <0.125 | <0.125 | 0.25 | 4 | 0.5 | 0.5 |
| +30% bovine serum | 8 | 1 | 1 | 1 | 1 | 1 | 1 | | 1 | 1 |
| 47 E coli SKF12140 | >32 | >128 | >128 | >128 | >128 | >128 | >128 | >128 | >128 | >128 |
| 145 Candida albicans SKF2270 | >32 | >128 | >128 | >128 | >128 | >128 | >128 | >128 | >128 | >128 |

| MICROORGANISM | COMPOUND N° | | | | | | | | | |
|---|---|---|---|---|---|---|---|---|---|---|
| | 47 | 49 | 50 | 56 | 80 | 81 | 82 | 103 | 108 | 123 | 125 |
| 819 Staph. aureus Smith | 0.25 | 0.06 | ≤0.125 | ≤0.125 | 0.125 | 0.125 | 0.125 | 0.5 | ≤0.125 | ≤0.125 | 0.25 |
| +30% bovine serum | 1 | 0.5 | 1 | 1 | 1 | 1 | 1 | 1 | 1 | 0.5 | 1 |
| 613 Staph. aureus clin. isolate Met-R | 0.5 | 0.25 | 0.25 | ≤0.125 | 0.5 | 0.5 | 0.5 | 1 | ≤0.125 | 0.25 | 0.5 |
| 3797 Staph. aureus clin. isolate VISA Met-R | 4 | 2 | 2 | 2 | 2 | 2 | 2 | 4 | 1 | 2 | 8 |
| 3798 Staph. aureus clin. isolate VISA | 2 | 1 | 1 | 1 | 1 | 1 | 1 | 2 | 0.5 | 2 | 2 |
| +30% bovine serum | 4 | 4 | 4 | 4 | 4 | 8 | 4 | 4 | 4 | 8 | 8 |
| 49 Strep. pyogenes C203 | ≤0.125 | ≤0.06 | ≤0.125 | ≤0.125 | ≤0.125 | ≤0.125 | ≤0.125 | ≤0.125 | ≤0.125 | ≤0.125 | ≤0.125 |
| 559 Entero. faecalis (isogenic of L 560) | 0.5 | 0.5 | 0.25 | ≤0.125 | 0.5 | 0.5 | 0.5 | 2 | ≤0.125 | 0.25 | 0.5 |
| 560 Entero. faecalis VanA | 1 | 0.5 | ≤0.125 | ≤0.125 | 0.25 | 0.25 | 0.5 | 1 | ≤0.125 | ≤0.125 | 0.25 |
| +30% bovine serum | 1 | 2 | 1 | 0.5 | 2 | 2 | 2 | 4 | 1 | 1 | 2 |
| 568 Entero. faecium (isogenic of L569) | nd | nd | 0.5 | 0.5 | nd | nd | nd | 2 | 0.25 | 0.5 | 1 |
| 569 Entero. faecium clin. isolate Van-A | 1 | 0.5 | 0.5 | 0.25 | 0.5 | 0.25 | 0.5 | 2 | ≤0.125 | ≤0.125 | 4 |
| +30% bovine serum | 8 | 4 | 4 | 2 | 8 | 8 | 4 | 8 | 2 | 4 | 4 |
| 47 E coli SKF12140 | >128 | >128 | >128 | >128 | >128 | >128 | >128 | >128 | >128 | >128 | >128 |
| 145 Candida albicans SKF2270 | >128 | >128 | >128 | >128 | >128 | >128 | >128 | >128 | >128 | >128 | >128 |

*n.a.: not available

As it is evident from the above TABLE 2 the new compounds falling within formula (Ia) in most cases show the same level of activity of the know compounds members of the ramoplanin family, i.e. compound 1, 5 and 35.

A further set of experiments for measuring the antimicrobial activity in vitro of a series of compounds of formula (Ia) in comparison with the known compound 1 was carried out directly on the solutions deriving from the reaction of the starting acid of formula (IV) with the deacyl ramoplanin of formula (III) according to the method A described in the Examples.

The reaction solutions (resulting from the addition of 1M hydrochloric acid as described in Method A) were diluted at 6000 mcg/ml by adding 0.1% peptone Difco Laboratories, (Detroit, Mich., USA) plus 0.9% NaCl (PBS). The resulting solutions were diluted with water at the desired concentration to perform the test that was then carried out in the same way described for the isolated compounds reported in Table 2.

The following TABLE 2.1 reports the results of the above described experiments.

TABLE 2.1

Microbiological activity (reaction solutions) MIC mcg/ml

Compound N°

| MICROORGANISM | 1 | 50 | 54 | 55 | 56 | 57 | 63 | 65 | 68 | 72 | 76 | 83 | 84 | 85 |
|---|---|---|---|---|---|---|---|---|---|---|---|---|---|---|
| 819 Staph. aureus Smith | ≦0.125 | 0.5 | 0.5 | 0.5 | 0.5 | 2 | 1 | 0.5 | 1 | 1 | 2 | 0.5 | 0.25 | 1 |
| +30% bovine serum | 2 | 1 | 2 | 2 | 1 | 2 | 2 | 2 | 2 | 2 | 0.25 | 1 | 2 | 1 |
| 613 Staph. aureus clin. isolate Met-R | 0.25 | 2 | 0.5 | 1 | 1 | 2 | 1 | 4 | 2 | 2 | 2 | 0.5 | 0.5 | 4 |
| 3797 Staph. aureus clin. isolate VISA Met-R | 2 | 8 | 4 | 8 | 16 | 16 | 8 | 4 | 8 | 8 | 8 | 4 | 8 | 16 |
| 3798 Staph. aureus clin. isolate VISA | 1 | 4 | 4 | 8 | 2 | 8 | 4 | 4 | 4 | 8 | 16 | 4 | 4 | 8 |
| +30% bovine serum | 8 | 4 | 8 | 8 | 16 | 4 | 16 | 16 | 32 | 4 | 8 | 8 | 8 | 8 |
| 49 Strep. pyogenes C203 | ≦0.125 | ≦0.125 | ≦0.06 | ≦0.06 | ≦0.125 | ≦0.125 | ≦0.125 | ≦0.125 | ≦0.125 | ≦0.125 | ≦0.125 | ≦0.06 | ≦0.06 | ≦0.06 |
| 559 Entero. faecalis (isogenic of L 560) | ≦0.125 | 2 | 0.5 | 1 | 1 | 4 | 0.5 | 0.25 | 0.25 | 4 | 4 | 0.5 | 0.5 | 1 |
| 560 Entero. faecalis VanA | ≦0.125 | 1 | 0.25 | 0.5 | 1 | 4 | 0.5 | 0.25 | 0.5 | 4 | 2 | 0.5 | 0.25 | 4 |
| +30% bovine serum | 2 | 2 | 2 | 2 | 4 | 8 | 2 | 4 | 4 | 4 | 4 | 4 | 2 | 4 |
| 568 Entero. faecium (isogenic of L569) | ≦0.125 | 2 | 1 | 2 | 1 | 8 | 1 | 0.5 | 1 | 8 | 4 | 1 | 1 | 2 |
| 569 Entero. faecium clin. isolate Van-A | ≦0.125 | 2 | 0.5 | 0.5 | 1 | 4 | 1 | 0.5 | 0.5 | 4 | 2 | 0.5 | 0.5 | 2 |
| +30% bovine serum | 2 | 4 | 4 | 8 | 4 | 16 | 8 | 8 | 16 | 16 | 8 | 4 | 4 | 8 |
| 47 E coli SKF12140 | >128 | >128 | >64 | >64 | >128 | >128 | >128 | >128 | >128 | >128 | >128 | >64 | >64 | >64 |
| 145 Candida albicans SKF2270 | >128 | >128 | >64 | >64 | >128 | >128 | >128 | >128 | >128 | >128 | >128 | >64 | >64 | >64 |

Compound N°

| MICROORGANISM | 86 | 87 | 88 | 89 | 90 | 91 | 92 | 93 | 94 | 95 | 96 | 97 | 98 | 99 |
|---|---|---|---|---|---|---|---|---|---|---|---|---|---|---|
| 819 Staph. aureus Smith | 4 | 2 | 1 | 1 | 1 | 2 | 2 | 0.5 | 2 | ≦0.125 | ≦0.125 | ≦0.125 | ≦0.125 | ≦0.125 |
| +30% bovine serum | 8 | 2 | 1 | 2 | 2 | 2 | 4 | 1 | 2 | 0.5 | 0.5 | 1 | 1 | 2 |
| 613 Staph. aureus clin. isolate Met-R | 2 | 4 | 0.5 | 1 | 4 | 4 | 2 | 2 | 2 | 0.5 | 0.25 | 0.5 | 0.25 | 0.5 |
| 3797 Staph. aureus clin. isolate VISA Met-R | 16 | 16 | 8 | 4 | 4 | 8 | 16 | 8 | 32 | 2 | 2 | 2 | 2 | 4 |
| 3798 Staph. aureus clin. isolate VISA | 16 | 8 | 4 | 2 | 16 | 4 | 8 | 4 | 8 | 2 | 2 | 2 | 2 | 2 |
| +30% bovine serum | 32 | 16 | 8 | 4 | 8 | 8 | 8 | 4 | 8 | 4 | 4 | 4 | 4 | 8 |
| 49 Strep. pyogenes C203 | ≦0.06 | ≦0.06 | ≦0.06 | ≦0.06 | ≦0.06 | ≦0.06 | ≦0.06 | ≦0.125 | ≦0.125 | ≦0.125 | ≦0.125 | ≦0.125 | ≦0.125 | ≦0.125 |
| 559 Entero. faecalis (isogenic of L 560) | 1 | 1 | 1 | 1 | 1 | 2 | 2 | 2 | 2 | 0.5 | 0.25 | 0.25 | ≦0.125 | 0.5 |
| 560 Entero. faecalis VanA | 2 | 1 | 1 | 1 | 0.5 | 2 | 2 | 1 | 2 | 0.25 | ≦0.125 | ≦0.125 | ≦0.125 | 0.25 |
| +30% bovine serum | 2 | 2 | 2 | 2 | 4 | 4 | 4 | 2 | 4 | 2 | 2 | 2 | 1 | 4 |
| 568 Entero. faecium (isogenic of L569) | 2 | 2 | 2 | 2 | 2 | 4 | 2 | 2 | 2 | 0.5 | 0.5 | 0.25 | 0.25 | 0.5 |
| 569 Entero. faecium clin. isolate Van-A | 2 | 2 | 2 | 1 | 1 | 4 | 2 | 2 | 4 | 0.5 | 0.5 | 0.25 | ≦0.125 | 0.5 |
| +30% bovine serum | 8 | 8 | 4 | 8 | 8 | 8 | 8 | 4 | 8 | 4 | 4 | 2 | 2 | 8 |
| 47 E coli SKF12140 | >64 | >64 | >64 | >128 | >128 | >64 | >64 | >128 | >128 | >128 | >128 | >128 | >128 | >128 |
| 145 Candida albicans SKF2270 | >64 | >64 | >64 | >128 | >128 | >64 | >64 | >128 | >128 | >128 | >128 | >128 | >128 | >128 |

TABLE 2.1-continued

Microbiological activity (reaction solutions) MIC mcg/ml

Compound N°

| MICROORGANISM | 100 | 101 | 102 | 103 | 104 | 105 | 106 | 107 | 108 | 109 | 110 | 111 | 112 | 113 |
|---|---|---|---|---|---|---|---|---|---|---|---|---|---|---|
| 819 *Staph. aureus* Smith | ≦0.125 | 2 | 2 | 2 | 1 | 8 | 0.5 | 0.5 | 0.5 | 4 | 16 | 1 | 0.125 | 0.25 |
| +30% bovine serum | 0.5 | 4 | 2 | 2 | 1 | 16 | 2 | 0.125 | 1 | 0.5 | 4 | 0.125 | 1 | 1 |
| 613 *Staph. aureus* clin. isolate Met-R | ≦0.125 | 4 | 2 | 4 | 2 | 16 | 1 | 0.5 | 0.5 | 4 | 16 | 1 | 0.5 | 2 |
| 3797 *Staph. aureus* clin. isolate VISA Met-R | 4 | 64 | 8 | 8 | 16 | 32 | 32 | 4 | 4 | 32 | 64 | 8 | 8 | 16 |
| 3798 *Staph. aureus* clin. isolate VISA | 0.5 | 8 | 8 | 16 | 4 | 16 | 8 | 8 | 8 | 32 | 64 | 16 | 4 | 8 |
| +30% bovine serum | 4 | 8 | 8 | 16 | 16 | 8 | 64 | 8 | 16 | 16 | 64 | 8 | 8 | 8 |
| 49 *Strep. pyogenes* C203 | ≦0.125 | ≦0.125 | ≦0.125 | ≦0.125 | ≦0.125 | ≦0.125 | ≦0.125 | ≦0.125 | ≦0.125 | ≦0.125 | 0.25 | ≦0.125 | ≦0.125 | ≦0.125 |
| 559 *Entero. faecalis* (isogenic of L 560) | ≦0.125 | 4 | 2 | 8 | 2 | 8 | 1 | 1 | 1 | 4 | 16 | 2 | 1 | 2 |
| 560 *Entero. faecalis* VanA | ≦0.125 | 8 | 2 | 8 | 8 | 8 | 1 | 0.5 | 0.5 | 4 | 16 | 2 | 1 | 2 |
| 568 *Entero. faecium* (isogenic of L569) | 1 | 8 | 8 | 8 | 4 | 16 | 4 | 4 | 4 | 8 | 32 | 4 | 2 | 4 |
| 569 *Entero. faecium* clin. isolate Van-A | 0.25 | 8 | 4 | 8 | 4 | 16 | 2 | 2 | 2 | 8 | 32 | 4 | 2 | 4 |
| +30% bovine serum | ≦0.125 | 8 | 4 | 8 | 4 | 8 | 1 | 1 | 1 | 8 | 16 | 2 | 1 | 2 |
| 47 *E coli* SKF12140 | 4 | 16 | 16 | 16 | 16 | 32 | 8 | 8 | 8 | 16 | 32 | 8 | 2 | 8 |
| 145 *Candida albicans* SKF2270 | >128 | >128 | >128 | >128 | >128 | >64 | >64 | >128 | >128 | >128 | >128 | >128 | >128 | >128 |
| | >128 | >128 | >128 | >128 | >128 | >64 | >64 | >128 | >128 | >128 | >128 | >128 | >128 | >128 |

COMPOUND N°

| MICROORGANISM | 114 | 115 | 116 | 117 | 118 | 119 | 120 | 121 | 122 | 124 | 125 | 126 | 127 |
|---|---|---|---|---|---|---|---|---|---|---|---|---|---|
| 819 *Staph. aureus* Smith | 0.125 | 0.125 | 0.25 | 1 | 2 | 2 | 4 | 0.5 | 1 | 0.5 | 1 | 1 | 0.5 |
| +30% bovine serum | 1 | 1 | 1 | 2 | 4 | 2 | 4 | 2 | 1 | 2 | 4 | 8 | 2 |
| 613 *Staph. aureus* clin. isolate Met-R | 1 | 1 | 1 | 2 | 2 | 4 | 4 | 0.5 | 4 | 2 | 4 | 4 | 1 |
| 3797 *Staph. aureus* clin. isolate VISA Met-R | 16 | 8 | 8 | 16 | 32 | 16 | 32 | 4 | 8 | 8 | 8 | 8 | 8 |
| 3798 *Staph. aureus* clin. isolate VISA | 4 | 4 | 8 | 8 | 16 | 8 | 16 | 4 | 8 | 4 | 8 | 8 | 4 |
| +30% bovine serum | 8 | 4 | 8 | 8 | 64 | 16 | 32 | 16 | 16 | 32 | 32 | >128 | 16 |
| 49 *Strep. pyogenes* C203 | ≦0.125 | ≦0.125 | ≦0.125 | ≦0.06 | ≦0.06 | ≦0.125 | ≦0.125 | ≦0.125 | ≦0.125 | ≦0.125 | 0.25 | ≦0.125 | ≦0.125 |
| 559 *Entero. faecalis* (isogenic of L 560) | 1 | 1 | 2 | 1 | 1 | 1 | 4 | 0.5 | 1 | 0.5 | 1 | 0.5 | 0.5 |
| 560 *Entero. faecalis* VanA | 1 | 1 | 2 | 2 | 2 | 1 | 4 | 0.25 | 1 | 0.5 | 1 | 0.25 | 0.5 |
| 568 *Entero. faecium* (isogenic of L569) | 2 | 2 | 4 | 4 | 4 | 4 | 8 | 2 | 4 | 4 | 4 | 8 | 2 |
| 569 *Entero. faecium* clin. isolate Van-A | 2 | 2 | 2 | 4 | 4 | 4 | 8 | 1 | 4 | 1 | 2 | 2 | 1 |
| +30% bovine serum | 4 | 1 | 2 | 4 | 2 | 1 | 4 | 0.25 | 2 | 1 | 1 | 1 | 0.5 |
| 47 *E coli* SKF12140 | 4 | 4 | 8 | 8 | 16 | 8 | 16 | 8 | 8 | 8 | 16 | 8 | 8 |
| 145 *Candida albicans* SKF2270 | >128 | >128 | >128 | >128 | >128 | >128 | >128 | >128 | >128 | >128 | >128 | >128 | >128 |
| | >128 | >128 | >128 | >128 | >128 | >128 | >128 | >128 | >128 | >128 | >128 | >128 | >128 |

It is evident from the above TABLE 2.1 that, as in the case of TABLE 2, the new compounds with formula (Ia) in most cases show the same level of activity of the known compound 1.

The antimicrobial activity of some compounds representative of the invention in comparison with ramoplanin was demonstrated through in vivo tests in rats.

As an example, therapeutical effectiveness of some representative compounds of formula (Ia) in murine septicaemia caused by intraperitoneally administered *Staphylococcus aureus* Smith SA 819 was evaluated in comparison with ramoplanin. Vancomycin was chosen as reference drug for the evaluation of in vivo antiinfective activity.

Mice were infected intraperitoneally with *Staphylococcus aureus* Smith SA 819. Untreated animals died within 24 hours after infection. Groups of eight mice each were treated s.c. with different dose levels of ramoplanin or of each test compound, starting 10–20 min after challenge. Reference drugs was s.c. injected vancomycin. The 50% effective dose ($ED_{50}$) and 95% confidence limits were calculated by the Spearman-Kärber (Finney, D. J. 1952. The Spearman-Kärber method, p. 524–530. In D. J. Finney (ed.), Statistical method in biological assay. Charles Griffin & Company Limited, London) method from the percentage of animals surviving to day 7 at each dose.

The experimental data are reported in the following TABLE 3.

TABLE 3

Efficacy of ramoplanin-like amide derivatives against *Staphylococcus aureus* Smith SA 819 systemic infection in mice

| Compound | Route | $ED_{50}$ (mg/kg/dose) | 95% confidence limits |
|---|---|---|---|
| Ramoplanin | s.c. | 0.51 | 0.38–0.68 |
| 13 | s.c. | 0.15 | 0.13–0.18 |
| 37 | s.c. | 0.34 | 0.26–0.44 |
| 39 | s.c. | 0.17 | 0.14–0.21 |
| 40 | s.c. | 0.17 | 0.14–0.21 |
| Vancomycin | s.c. | 0.64 | 0.53–0.77 |

As it can be seen from the above data, compounds 13, 37, 39, 40, which are falling within formula (Ia), show better efficacy with respect to ramoplanin and the reference drug vancomycin.

A confirmation of the superior antimicrobial activity of the above mentioned compounds 39 and 40 in comparison with ramoplanin was given in a further experiments carried out in mice imfected with *Staphylococcus aureus* AS613, a MRSA strain less susceptible in vivo to ramoplanin than *Staphylococcus aureus* Smith SA 819.

Mice were infected intraperitoneally with ca $10^7$ CFU/mouse of *Staphylococcus aureus* SA 613. Untreated animals died within 24 hours after infection. Groups of eight mice each were treated iv or s.c. with different dose levels of ramoplanin or each test compound, starting 10–20 minutes after challenge. Ramoplanin and vancomycin were used as reference drugs.

The 50% effective dose ($ED_{50}$), the 95% confidence limits, calculated by the Spearman-Kärber method from the percentages of animals surviving to day 7 at each dose of the four test compounds, ramoplanin and vancomycin are reported in TABLE 4.

TABLE 4

Efficacy of ramoplanin-like amide derivatives against methicillin-resistant *Staphylococcus aureus* SA 613 in murine infection

| Compound | Route | $ED_{50}$ (mg/kg/dose) | 95% confidence limits |
|---|---|---|---|
| Ramoplanin | i.v. | 4.02 | 3.28–4.94 |
|  | s.c. | >125 |  |
| 39 | i.v. | 1.61 | 1.39–1.87 |
|  | s.c. | 3.20 | 2.73–3.76 |
| 40 | i.v. | 3.20 | 2.73–3.76 |
|  | s.c. | 11.28 | 9.15–13.91 |
| Vancomycin | s.c. | 8 | 6.81–9.39 |

The tolerability of the novel ramoplanin-like amide derivatives of formula (Ia) in comparison with ramoplanin has been studied by measuring the haemolytic potential on blood cells according to the method suggested in the literature (D. Salauze and D. Decouvelare "In vitro assessment of the haemolytic potential of candidate drugs", Comp. Haematology Intern. 1994; G. Dal Negro and P. Cristofori, "A new approach for evaluation of the in vitro haemolytic potential of solution of a new medicine", Comp. Hematology Intern. 1996).

The ramoplanin-like amide derivatives were dissolved at 40.000 mcg/ml in dimethyl sulfoxide (DMSO) and then diluted 1:5 in 0.1% peptone Difco Laboratories, (Detroit, Mich., USA) plus 0.9% NaCl (PBS).

Whole blood sample was obtained from the dorsal aorta of rats and diluted 1:100 in PBS before the test.

Test groups included:

Group 1—ramoplanin and ramoplanin-like amide derivatives at concentrations reported in TABLE 5

Group 2—PBS as physiologic haemolysis control

Group 3—saponin (Sigma), solution at 3% in distilled water, as 100% haemolysis control.

The test groups were diluted 1:5 in blood cells and incubated in water bath at 37° C. for 45 minutes.

After the incubation time the samples were centrifuged at 2500–3000 g for 10 minutes, and 0.1 ml of each supernatant was diluted in 900 mcl of Drabkin's reagent (Sigma).

The optical density (OD) of the samples was measured at 540 nm versus a blank preparation of Drabkin's reagent plus 0.1 ml of PBS.

The test was performed in triplicate.

The percentage of haemolysis was calculate using the formula $$\Delta x/\Delta t \times 100 = \% \text{ of haemolysis}$$

$\Delta x$=mean value of $OD_{540}$ for each concentration tested (GROUP 1–2)

$\Delta t$=mean value of $OD_{540}$ for 100% haemolysis control (GROUP 3).

The haemolysis was considered significant when exceeding at least 3 times the haemolytic value of blank control (GROUP 2).

The results are reported in TABLE 5

TABLE 5

Haemolytic effect (isolated compounds)

| Compound N° | % lysis at 1600 mcg/ml | % lysis at 1200 mcg/ml | % lysis at 800 mcg/ml | % lysis at 600 mcg/m | % lysis at 400 mcg/ml | % lysis at 300 mcg/ml | % lysis at 200 mcg/ml | % lyis at 100 mcg/ml | % Lysis PBS | Significative value |
|---|---|---|---|---|---|---|---|---|---|---|
| Ramoplanin | n.a.[1] | n.a.[1] | n.a.[1] | n.a.[1] | 100 | n.a.[1] | 100 | 100 | 2.27 | ≧6.8 |
| 1 | n.a.[1] | n.a.[1] | n.a.[1] | n.a.[1] | 100 | n.a.[1] | 100 | 86.04 | 2.27 | ≧6.8 |
| 4 | n.a.[1] | n.a.[1] | n.a.[1] | n.a.[1] | 58.69 | n.a.[1] | 4.56 | n.a.[1] | 2.27 | ≧6.8 |
| 10 | n.a.[1] | n.a.[1] | n.a.[1] | n.a.[1] | 0.57 | n.a.[1] | n.a.[1] | n.a.[1] | 2.27 | ≧6.8 |
| 12 | n.a.[1] | n.a.[1] | 58.82 | n.a.[1] | 67.04 | n.a.[1] | 58.82 | 51.86 | 8.85 | ≧26.55 |
| 13 | 93.92 | n.a.[1] | 94.23 | n.a.[1] | 83.24 | n.a.[1] | 17.18 | n.a. | 0.9. | ≧2.75 |
| 14 | n.a.[1] | n.a.[1] | n.a.[1] | n.a.[1] | 1.71 | n.a.[1] | n.a.[1] | 2.85 | 2.27 | ≧6.8 |
| 15 | n.a.[1] | 8.5 | n.a.[1] | 10.9 | n.a.[1] | 2.0 | n.a.[1] | n.a.[1] | 0 | 0 |
| 23 | n.a.[1] | n.a.[1] | n.a.[1] | n.a.[1] | 3.99 | n.a.[1] | n.a.[1] | n.a.[1] | 2.27 | ≧6.8 |
| 24 | n.a.[1] | n.a.[1] | n.a.[1] | n.a.[1] | 86.32 | n.a.[1] | 5.98 | 2.85 | 2.27 | ≧6.8 |
| 32 | n.a.[1] | n.a.[1] | n.a.[1] | n.a.[1] | 74.25 | n.a.[1] | 26.03 | 9.48 | 10.9 | ≧32.7 |
| 34 | n.a.[1] | n.a.[1] | n.a.[1] | n.a.[1] | n.a.[2] | n.a.[1] | 16.91 | 17.73 | 10.9 | ≧32.7 |
| 35 | n.a.[1] | n.a.[1] | n.a.[1] | n.a.[1] | 92.82 | n.a.[1] | 80.44 | 58.99 | 10.9 | ≧32.7 |
| 37 | 98.52 | n.a.[1] | 96.68 | n.a.[1] | 34.65 | n.a.[1] | 36.30 | 28.05 | 10.9 | ≧32.7 |
| 38 | n.a.[1] | n.a.[1] | n.a.[1] | n.a.[1] | 4.58 | n.a.[1] | 2.54 | 1.53 | 2.8 | ≧8.4 |
| 39 | 20.8 | n.a.[1] | 7.1 | n.a.[1] | 4.07 | n.a.[1] | 2.04 | 1.02 | 2.8 | ≧8.4 |
| 40 | 82.7 | n.a.[1] | 72.6 | n.a.[1] | 13.74 | n.a.[1] | n.a.[1] | n.a.[1] | 2.8 | ≧8.4 |
| 47 | n.a.[1] | 44.9 | n.a.[1] | 3.6 | n.a.[1] | 1.7 | n.a.[1] | n.a.[1] | 0.7 | ≧2.1 |
| 49 | 69.3 | n.a.[1] | 32.7 | n.a.[1] | 8.9 | n.a.[1] | n.a.[1] | n.a.[1] | 0.7 | ≧2.1 |
| 50 | n.a.[1] | 4.5 | n.a.[1] | 0 | n.a.[1] | 0 | n.a.[1] | n.a.[1] | 0 | 0 |
| 56 | n.a.[1] | 51.6 | n.a.[1] | 4.9 | n.a.[1] | 3.3 | n.a.[1] | n.a.[1] | 0 | 0 |
| 80 | n.a.[1] | 70.6 | n.a.[1] | 69.6 | n.a.[1] | 45.9 | n.a.[1] | n.a.[1] | 0.7 | ≧2.1 |
| 81 | n.a.[1] | 79.2 | n.a.[1] | 73.6 | n.a.[1] | 74.6 | n.a.[1] | n.a.[1] | 0.7 | ≧2.1 |
| 82 | n.a.[1] | 75.6 | n.a.[1] | 1.3 | n.a.[1] | 0.7 | n.a.[1] | n.a.[1] | 0.7 | ≧2.1 |
| 103 | n.a.[1] | 0 | n.a.[1] | 0 | n.a.[1] | 0.8 | n.a.[1] | n.a.[1] | 0 | 0 |
| 108 | n.a.[1] | 86.6 | n.a.[1] | 18.3 | n.a.[1] | 0 | n.a.[1] | n.a.[1] | 0 | 0 |
| 123 | n.a.[1] | 84.6 | n.a.[1] | 22.4 | n.a.[1] | 4.5 | n.a.[1] | n.a.[1] | 0 | 0 |
| 125 | n.a.[1] | 65.4 | n.a.[1] | 2.8 | n.a.[1] | 2.4 | n.a.[1] | n.a.[1] | 0 | 0 |

[1]n.a. = not available

Among the tested compounds resulted particularly interesting for the absence of haemolytic activity: 39 at 800 mcg/ml, 47 and 82 at 600, 10, 14, 23 and 38 at 400 mcg/ml, 4, 24, 32 and 34 at 200 mcg/ml.

Also compound 40 showed a particularly low haemolytic activity (13,74% at 400 mcg/ml), which makes it interesting for use in therapy.

A further set of experiments for measuring the haemolytic effect of a series of compounds of formula (Ia) in comparison with the known compound 1 was carried out directly on the solutions deriving from the reaction of the starting acid of formula (IV) with the deacyl ramoplanin of formula (III) according to the method A described in the Examples.

The reaction solutions (resulting from the addition of 1M hydrochloric acid as described in Method A) were diluted at 1200 mcg/ml by adding 0.1% peptone Difco Laboratories, (Detroit, Mich., USA) plus 0.9% NaCl (PBS). The test was then carried out in the same way described for the isolated compounds reported in Table 5.

The following TABLE 5.1 reports the results of the above described experiments.

TABLE 5.1

Haemolytic effect (reaction solutions)

| Compound N° | % lysis at 1200 mcg/ml | % lysis at 600 mcg/m | % lysis at 300 mcg/ml | % Lysis PBS | Significative value |
|---|---|---|---|---|---|
| 1 | n.a.[1] | 88.87 | 74.39 | 3.98 | ≧12 |
| 50 | 77.3 | 40.1 | 6.20 | 0.4 | ≧1.2 |
| 54 | 87.2 | 70.5 | 63.6 | 0 | 0 |
| 55 | 70.5 | 71.3 | 0 | 0 | 0 |
| 56 | 55.0 | 53.2 | 8.8 | 0 | 0 |
| 57 | 71.3 | 0 | 0 | 0 | 0 |
| 63 | 91.7 | 87.4 | 11.7 | 0 | 0 |
| 65 | 82.6 | 70.9 | 2.3 | 0 | 0 |
| 68 | 81.0 | 32.2 | 0 | 0 | 0 |
| 72 | 43.3 | 1.2 | 0 | 0 | 0 |
| 76 | 80.6 | 0 | 0 | 0 | 0 |
| 83 | 80.2 | 47.7 | 1.6 | 0 | 0 |
| 84 | 62.0 | 58.9 | 5.0 | 0 | 0 |
| 85 | 70.5 | 62.0 | 28.7 | 0 | 0 |
| 86 | 99.2 | 83.5 | 37.8 | 1.8 | ≧5.5 |
| 87 | 86.6 | 98.2 | 6.3 | 1.8 | ≧5.5 |
| 88 | 71.4 | 85.6 | 4.2 | 1.8 | ≧5.5 |
| 89 | 97.6 | 99.2 | 4.7 | 1.8 | ≧5.5 |
| 90 | 90.8 | 95.5 | 3.1 | 1.8 | ≧5.5 |
| 91 | 95.0 | 2.6 | 0 | 1.8 | ≧5.5 |
| 92 | 90.8 | 10.5 | 0 | 1.8 | ≧5.5 |
| 93 | 84.6 | 73.6 | 16.5 | 0.4 | ≧1.2 |
| 94 | 2.9 | 7.0 | 5.4 | 0.4 | ≧1.2 |
| 95 | 90.2 | 40.9 | 7.4 | 0.4 | ≧1.2 |
| 96 | 95.9 | 81.9 | 15.7 | 0.4 | ≧1.2 |
| 97 | 87.7 | 83.5 | 12.8 | 0.4 | ≧1.2 |
| 98 | 76.9 | 80.2 | 15.3 | 0.4 | ≧1.2 |
| 99 | 86.4 | 73.6 | 16.5 | 0.4 | ≧1.2 |
| 101 | 45.6 | 0.6 | 0 | 0 | 0 |
| 102 | 64.3 | 0 | 0 | 0 | 0 |
| 103 | 6.1 | 0 | 0 | 0 | 0 |
| 104 | 32.5 | 26.6 | 0 | 0 | 0 |

TABLE 5.1-continued

Haemolytic effect (reaction solutions)

| Compound N° | % lysis at 1200 mcg/ml | % lysis at 600 mcg/m | % lysis at 300 mcg/ml | % Lysis PBS | Significative value |
|---|---|---|---|---|---|
| 105 | 1.3 | 0 | 0 | 0 | 0 |
| 106 | 68.8 | 39.7 | 8.4 | 0 | 0 |
| 107 | 64.7 | 48.8 | 2.0 | 0 | 0 |
| 108 | 69.2 | 0 | 0 | 0 | 0 |
| 109 | 27.9 | 0 | 0 | 0 | 0 |
| 110 | 52.7 | 0 | 0 | 0 | 0 |
| 111 | 1 | 0 | 0 | 0 | 0 |
| 112 | 57.7 | 0 | 0 | 0 | 0 |
| 113 | 5.8 | 0 | 0 | 0 | 0 |
| 114 | 57.2 | 0 | 0 | 0 | 0 |
| 115 | 61.7 | 7.0 | 0 | 0 | 0 |
| 116 | 0 | 0 | 0 | 0 | 0 |
| 117 | 16.7 | 0 | 0 | 0 | 0 |
| 118 | 70.5 | 0 | 0 | 0 | 0 |
| 119 | 79.1 | 10.5 | 0 | 0 | 0 |
| 120 | 0 | 0 | 0 | 0 | 0 |
| 121 | 100 | 63.9 | 0 | 0 | 0 |
| 122 | 72.6 | 0 | 0 | 0 | 0 |
| 123 | 0.9 | 0.4 | 0 | 0 | 0 |
| 124 | 90.4 | 93.5 | 77.4 | 0 | 0 |
| 125 | 95.2 | 92.6 | 9.6 | 0 | 0 |
| 126 | 88.8 | 77.9 | 28.7 | 0 | 0 |
| 127 | 97.8 | 88.3 | 0 | 0 | 0 |

Practically all tested compounds resulted less haemolytic than the known reference compound 1.

Among the tested compounds, the compounds 57, 72, 76, 91, 94, 101, 102, 103, 105, 108, 109, 110, 111, 112, 113, 114, 115, 116, 117, 118, 120, 122, 123 showed a particularly low haemolytic effect since their % lysis values at 600 mcg/ml is lower than 10%.

A further confirmation of the tolerability of the ramoplanin-like amide derivatives of formula (Ia) above was given by an in vivo study performed on compounds, 13, 37, 39 and 40.

The test compounds were solubilized at the required concentrations in 5% glucose. 3–6 rats for test compound for dose were treated at 24-hourly intervals for 1–2 days. Observation of the injection sites and general behaviour were recorded daily; urine was examined for presence of blood. Rats were killed 24–48 hours after the last treatment.

In the present experiment, ramoplanin has not been utilized, because several previous studies have clearly indicated that, at dosages similar to or slightly lower than those used in the present study, it caused serious local intolerability. Therefore, only a positive control, constituted by three rats given 5% glucose, was used as reference for all parameters.

Two dosages were tested, 10 and 20 mg/kg, each at different drug concentration (2, 4 or 8 mg/ml). First bolus was at 10 mg/kg-8 mg/ml. In case of positive result, other rats were immediately dosed with the same test compound at 20 mg/mg-8 mg/ml, that was the highest dose-concentration tested in this experimental phase. In case of negative result at 10 mg/kg-8 mg/ml, the same dose administered at a lower concentration (10 mg/kg-4 mg/ml or 10 mg/kg-2 mg/ml) was tested. When a positive result was found, the corresponding higher dose as mg/kg at the same drug concentration was assessed. With this experimental design it was possible to verify different conditions, and, at the same time, to determine the influence of the drug concentration vs the dose on the tolerability.

The following TABLE 6 summarize the results of this study.

TABLE 6

Summary of in vivo tolerability data of ramoplanin-like amide derivatives

| Test compounds | Treatment (dosage [mg/kg] - drug concentration [mg/mL]) | | | |
|---|---|---|---|---|
| | 10-8 | 10-4 | 20-4 | 20-8 |
| 13 | Haematuria | | | |
| | 3/3 rats P | 2/3 rats A | 2/3 rats A Taiis | Not tested |
| | 3/3 rats N | 3/3 rats N | 1/3 rats I General status | |
| 37 | 3/3 rats N | 3/3 rats N | 1/3 rats S Haematuria | |
| | 5/6 rats P | 2/3 rats A | 2/3 rats A Tails | Not tested |
| | 6/6 rats N | 3/3 rats N | 2/3 rats I General status | |
| 39 | 6/6 rats N | 3/3 rats N | 3/3 rats N Haematuria | |
| | 3/3 rats A | Not tested | Not tested Tails | 3/3 rats A |
| | 3/3 rats N | | General status | 3/3 rats N |
| 40 | 3/3 rats N | | Haematuria | 3/3 rats N |
| | 3/3 rats P | 3/3 rats A | 3/3 rats A Tails | Not tested |
| | 3/3 rats N | 3/3 rats N | 3/3 rats N General status | |
| | 3/3 rats N | 3/3 rats N | 3/3 rats N | |

Legend:
Haematuria: P = presence, A = absence;
tails: N = normal; I = signs of irritation;
general status: N = normal; S = suffering In view of the above reported antimicrobial activity and tolerability, the novel compounds of formula (Ia) of the present invention can effectively be employed as the active ingredients of the antimicrobial preparations used in human and veterinary medicine for the prevention and treatment of infectious diseases caused by pathogenic bacteria which are susceptible to said active ingredients, in particular, for the treatment of infections caused by *Enterococci, Streptococci and Staphylococci* strains.

The compounds of the present invention can be administered orally, topically or parenterally, the parenteral administration route being preferred.

Depending on the route of administration, these compounds can be formulated into various dosage forms. Preparations for oral administration may be in the form of capsules, tablets, liquid solutions or suspensions. As known in the art, the capsules and tablets may contain in addition to the active ingredient, conventional excipients such as diluents, e.g. lactose, calcium phosphate, sorbitol and the like, lubricants, e.g. magnesium stearate, talc, polyethylene glycol, binding agents, e.g. polyvinylpyrrolidone, gelatin, sorbitol, tragacanth, acacia, flavoring agents, and acceptable disintegrating and wetting agents. The liquid preparations, generally in the form of aqueous or oily solutions or suspensions, may contain conventional additives such as suspending agents.

For topical use the compounds of formula (Ia) of the present invention may also be prepared in suitable forms for absorption through the mucous membranes of the nose and throat or bronchial tissues and may conveniently take the form of liquid sprays or inhalants, lozenges, or throat paints.

For medication of the eyes, the preparation may be presented in liquid or semi-liquid form. Topical applications may be formulated in hydrophobic or hydrophilic bases as ointments, creams, lotions, paints, or powders.

For rectal administration the compounds of formula (Ia) of the invention are administered in the form of suppositories admixed with conventional vehicles, such as, for example, cocoa butter, wax, spermaceti or polyethyleneglycols and their derivatives.

Compositions for injection may take such forms as suspensions, solutions, or emulsions in oily or aqueous vehicles, and may contain formulatory agents such as suspending, stabilizing and/or dispersing agents.

Alternatively, the active ingredient may be in powder form for reconstitution at the time of delivery with a suitable vehicle, such as sterile water.

The amount of active principle to be administered depends on various factors such as the size and conditions of the subject to be treated, the route and frequency of administration, and the causative agent involved.

The compounds of the invention are generally effective at a dosage comprised between about 1 and about 40 mg of active ingredient per Kg of body weight. Depending on the characteristics of the specific compound, the infection and the patients, the effective dose can be administered in a single administration per day or divided in 2 to 4 administrations per day. Particularly desirable compositions are those prepared in the form of dosage units containing from about 30 to about 500 mg per unit.

EXAMPLES

General Procedure for the Synthesis of the Ramoplanin-like Amide derivatives.

Method A:

To a solution of the deacyl ramoplanin of formula (III), suitably protected at the (4,10) ornitine residues (4,10-protected RAMO-NH$_2$) (0.35 mmol), TEA (1.05 mmol) and the carboxylic acid R—COOH (IV) (0.525 mmol) in DMF (12.5 ml), PyBOP (0.525 mmol) is added with stirring at room temperature. The reaction is monitored by HPLC analysis (see the retention times in TABLE 7). The mixture is allowed to react at room temperature and, after 5 hours, piperidine (625 µl) or, alternatively, 2,2,6,6-tetramethylpiperidine (1.875 ml) is added to remove the protecting group from the ornitine moieties. The reaction is maintained under stirring at room temperature and monitored by HPLC (see the retention times in TABLE 7) and after 30 minutes diluted HCl is added (6.5 ml of a 1M solution). The desired product can be obtained by purification by preparative HPLC and lyophilisation. The derivative are characterized by $^1$H-NMR (TABLE 8), $^{13}$C-NMR and MS spectrometry (TABLE 9).

Method B:

To a solution of 4,10-protected RAMO-NH$_2$ (0.35 mmol) in DMF (12.5 ml), triethylamine (0.70 mmol) and the activated ester (0.35 mmol) is added with stirring at room temperature. The reaction is monitored by HPLC analysis (see the retention times in TABLE 7). The mixture is allowed to react at room temperature and after 5 hours piperidine (625 µl) or, alternatively, 2,2,6,6-tetramethylpiperidine (1.875 ml) is added to remove the protecting group from the ornitine moieties. The reaction is maintained under stirring at room temperature and monitored by HPLC (see the retention times in TABLE 7) and after 30 minutes diluted HCl is added (6.5 ml of a 1M solution). The desired product can be obtained by purification by preparative HPLC and lyophilisation. The derivative is characterized by $^1$H-NMR (TABLE 8), $^{13}$C-NMR and MS spectrometry (TABLE 9).

General Procedure to Prepare the Activated Esters

To a solution of the selected carboxylic acid R—COOH IV (2 mmol) and pentafluorophenol trifluoroacetate (2.32 mmol) in DMF (4 ml), pyridine (2.2 mmol) was added with stirring at room temperature. The reaction was monitored by TLC analysis. The mixture was allowed to react for 1 hour and then diluted with Ethylacetate (250 ml). The organic phase was washed with HCl 0.1 N, NaHCO$_3$ (5% solution) and water. The organic extracts were dried over sodium sulfate, filtered and the solvent removed under reduced pressure.

In the following TABLE 7 are summarized the compounds prepared, the method of manufacture and the starting material employed according to the general procedures described above.

TABLE 7

| Starting Compounds | | | | RT* | RT* | Final compounds (I) | |
|---|---|---|---|---|---|---|---|
| (III) | (IV) | | | Protected | Final | | |
| X = | Y' = | N° and structure | Method | compound | compound | N° | R = |
| MM | FMOC | 1a [structure: CH$_3$-CH(CH$_3$)-CH$_2$-CH=CH-CH=CH-COOH] | A | 34.2$^b$ | 10.9$^b$ | 1 | [structure] |

TABLE 7-continued

Compounds prepared according to the examples

| Starting Compounds | | | | RT* Protected compound | RT* Final compound | Final compounds (I) | |
|---|---|---|---|---|---|---|---|
| (III) | | (IV) | | | | | |
| X = | Y' = | N° and structure | Method | | | N° | R = |
| MM | FMOC | 2a  H$_3$C–CH$_2$–CH$_2$–COOH | A | 18.6$^d$ | 4$^d$ | 2 | H$_3$C–CH$_2$–CH$_2$–CH$_2$– |
| MM | FMOC | 3a  H$_3$C–(CH$_2$)$_3$–COOH | A | 21.3$^d$ | 4.51$^d$ | 3 | H$_3$C–(CH$_2$)$_4$– |
| MM | FMOC | 4a  H$_3$C–(CH$_2$)$_4$–COOH | A | 33.7$^b$ | 8.9$^b$ | 4 | H$_3$C–(CH$_2$)$_5$– |
| MM | FMOC | 5a  H$_3$C–(CH$_2$)$_5$–COOH | A | 24.7$^d$ | 5.5$^d$ | 5 | H$_3$C–(CH$_2$)$_6$– |
| MM | FMOC | 6a  H$_3$C–(CH$_2$)$_6$–COOH | A | 26.3$^d$ | 8.4$^d$ | 6 | H$_3$C–(CH$_2$)$_7$– |
| MM | FMOC | 7a  H$_3$C–(CH$_2$)$_7$–COOH | A | 27.5$^d$ | 12.7$^d$ | 7 | H$_3$C–(CH$_2$)$_8$– |
| MM | FMOC | 8a  C$_6$H$_5$–COOH | A | 17.1$^d$ | 8.4$^d$ | 8 | C$_6$H$_5$– |
| MM | FMOC | 9a  H$_3$C–C$_6$H$_4$–COOH | A | 20.9$^d$ | 4.2$^d$ | 9 | H$_3$C–C$_6$H$_4$– |
| MM | FMOC | 10a  H$_3$C–CH$_2$–O–C$_6$H$_4$–COOH | A | 32.4$^b$ | 5.6$^b$ | 10 | H$_3$C–CH$_2$–O–C$_6$H$_4$– |

TABLE 7-continued

Compounds prepared according to the examples

| Starting Compounds | | | | RT* Protected compound | RT* Final compound | Final compounds (I) | |
|---|---|---|---|---|---|---|---|
| (III) X = | Y' = | (IV) N° and structure | Method | | | N° | R = |
| MM | FMOC | 11a  NC—⌬—COOH | A | 17.3[d] | 3.85[d] | 11 | NC—⌬—CH3 |
| MM | FMOC | 12a  biphenyl-COOH | A | 34.3[b] | 11.8[b] | 12 | biphenyl-CH3 |
| MM | FMOC | 13a  naphthyl-CH2-COOH | A/B | 33.7[b] | 7.7[b] | 13 | naphthyl-CH2- |
| MM | CBZ | 13a  naphthyl-CH2-COOH | A/B | n.a. | 7.7[b] | 13 | naphthyl-CH2- |
| MM | FMOC | 14a  Ph-CH2-COOH | A | 30.2[b] | 4.2[b] | 14 | Ph-CH2- |
| MM | FMOC | 15a  H3C—⌬—CH2-COOH | A | 21.6[d] | 4.5[d] | 15 | H3C—⌬—CH2- |
| MM | FMOC | 16a  F—⌬—CH2-COOH | A | 20.2[d] | 4.13[d] | 16 | F—⌬—CH2- |

TABLE 7-continued

Compounds prepared according to the examples

| Starting Compounds | | | | RT* Protected compound | RT* Final compound | Final compounds (I) | |
|---|---|---|---|---|---|---|---|
| (III) | (IV) | | | | | | |
| X = | Y' = | N° and structure | Method | | | N° | R = |
| MM | FMOC | 17a  4-Cl-C6H4-CH2-COOH | A | 20.0[d] | 4.9[d] | 17 | 4-Cl-C6H4-CH2- |
| MM | FMOC | 18a  4-Br-C6H4-CH2-COOH | A | 22.4[d] | 4.95[d] | 18 | 4-Br-C6H4-CH2- |
| MM | FMOC | 19a  C6H5-CH2-CH2-COOH | A | 21.4[d] | 4.5[d] | 19 | C6H5-CH2-CH2- |
| MM | FMOC | 20a  C6H5-O-CH2-COOH | A | 20.7[d] | 4.15[d] | 20 | C6H5-O-CH2- |
| MM | FMOC | 21a  C6H5-CH2-CH2-CH2-COOH | A | 22.5[d] | 5[d] | 21 | C6H5-CH2-CH2-CH2- |
| MM | FMOC | 22a  H3C-CH2-CH2-O-(4-C6H4)-COOH | A | 25.2[d] | 5.6[d] | 22 | H3C-CH2-CH2-O-(4-C6H4)-CH2- |
| MM | FMOC | 23a  H3C-CH2-CH2-CH=CH-COOH | A | 31.4[b] | 5.2[b] | 23 | H3C-CH2-CH2-CH=CH- |
| MM | FMOC | 24a  H3C-CH2-CH2-CH2-CH2-CH=CH-COOH | A | 33.9[b] | 11.7[b] | 24 | H3C-CH2-CH2-CH2-CH2-CH=CH- |
| MM | FMOC | 25a  H3C-CH=CH-CH=CH-COOH | A | n.a. | 4.3[d] | 25 | H3C-CH=CH-CH=CH- |

TABLE 7-continued

Compounds prepared according to the examples

| Starting Compounds | | | | RT* Protected compound | RT* Final compound | Final compounds (I) | |
|---|---|---|---|---|---|---|---|
| (III) | | (IV) | | | | | |
| X = | Y' = | N° and structure | Method | | | N° | R = |
| MM | FMOC | 26a  *3-methylbenzoic acid (COOH with m-CH₃)* | A | 18.6[d] | 4[d] | 26 | *m-tolyl (phenyl with m-CH₃)* |
| MM | FMOC | 27a  *1-naphthoic acid* | A | 20.9[d] | 20.9[d] | 27 | *1-methylnaphthalene* |
| MM | FMOC | 28a  *2-naphthoic acid* | A | 22.1[d] | 4.9[d] | 28 | *2-methylnaphthalene* |
| MM | FMOC | 29a  *2-naphthylacetic acid* | A | 22.6[d] | 5[d] | 29 | *2-naphthylethyl* |
| MM | FMOC | 30a  *4-biphenylacetic acid* | A | 24.3[d] | 5.4[d] | 30 | *4-biphenylethyl* |
| MM | FMOC | 31a  *4-methylpentanoic acid (isocaproic acid)* | A | 20.5[d] | 4.13[d] | 31 | |
| MM | FMOC | 32a  *sorbic-type hexadienoic acid (CH₃-CH₂-CH₂-CH=CH-CH=CH-COOH)* | A | 33.9[b] | 9.6[b] | 32 | |

TABLE 7-continued

Compounds prepared according to the examples

| Starting Compounds | | | | RT* Protected compound | RT* Final compound | Final compounds (I) | |
|---|---|---|---|---|---|---|---|
| (III) X = | (IV) Y' = | N° and structure | Method | | | N° | R = |
| MM | FMOC | 33a  H₃C-CH(CH₃)-CH₂-CH=CH-CH=CH-COOH | A | 34.2[b] | 13.7[b] | 33 | |
| MM | FMOC | 34a  (CH₃)₂CH-CH=CH-CH=CH-COOH | A | 33.7[b] | 9.5[b] | 34 | |
| MM | FMOC | 35a  H₃C-CH₂-CH₂-CH=CH-CH=CH-COOH | A | 33.6[b] | 8[b] | 35 | |
| MM | FMOC | 36a  (CH₃)₂CH-CH=CH-CH=CH-COOH | A | 33.8[b] | 8.2[b] | 36 | |
| MM | FMOC | 37a  H₃C-CH₂-CH=CH-CH=CH-COOH | A | 33.2[b] | 5.5[b] | 37 | H₃C-CH₂-CH=CH-CH=CH- |
| MM | FMOC | 38a  2-methylbenzoic acid (o-toluic acid) | A | 18.9[a] | 16.27[c] | 38 | |
| MM | FMOC | 39a  2-methylphenylacetic acid | A/B | 21.7[a] | 18.83[c] | 39 | |

TABLE 7-continued
Compounds prepared according to the examples
| Starting Compounds | | | | RT* Protected | RT* Final | Final compounds (I) | |
|---|---|---|---|---|---|---|---|
| (III) | (IV) | | | | | | |
| X = | Y' = | N° and structure | Method | compound | compound | N° | R = |
| MM | CBZ | 39a 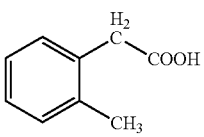 | A/B | n.a. | 18.83ᶜ | 39 | |
| MM | CBZ | 40a 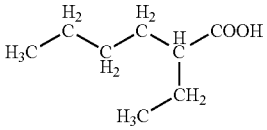 | A | n.a. | 21.73ᶜ | 40 | |
| MM | FMOC | 40a 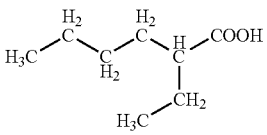 | A | 25.0ᵃ | 21.73ᶜ | 40 | |
| H | FMOC | 39a 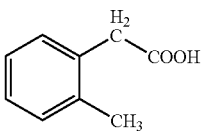 | A/B | n.a. | 25.83ᵍ | 43 | |
| MM | FMOC | 47a 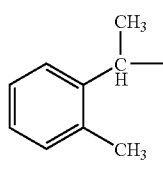 | A | 11.3ᵉ<br>12.0ᵉ | 17.3ᶠ<br>18.9ᶠ | 47 | 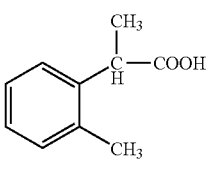 |
| MM | FMOC | 49a 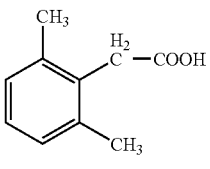 | A | 10.9ᵉ | 19.0ᶠ | 49 | |

TABLE 7-continued

Compounds prepared according to the examples

| Starting Compounds | | | | RT* | RT* | Final compounds (I) | |
|---|---|---|---|---|---|---|---|
| (III) | (IV) | | | Protected | Final | | |
| X = | Y' = | N° and structure | Method | compound | compound | N° | R = |
| MM | FMOC | 50a (3-methylbenzyl-CH₂-COOH structure) | A | 10.4$^e$ | 17.9$^f$ | 50 | |
| MM | FMOC | 54a (cinnamic acid, PhCH=CH-COOH) | A | 10.4$^e$ | 18.5$^f$ | 54 | |
| MM | FMOC | 55a (PhO-CH₂-CH₂-CH₂-COOH) | A | 11.3$^e$ | 18.9$^f$ | 55 | |
| MM | FMOC | 56a (2-CF₃-benzyl-CH₂-COOH) | A | 11.1$^e$ | 19.7$^f$ | 56 | |
| MM | FMOC | 57a (2-methoxy-benzyl-CH₂-COOH) | A | 9.8$^e$ | 16.2$^f$ | 57 | |
| MM | FMOC | 63a (branched alkyl carboxylic acid) | A | 12.9$^e$ | 22.4$^f$ | 63 | (branched alkyl structure) |
| MM | FMOC | 65a (branched alkyl carboxylic acid) | A | 13.2$^e$ | 23.2$^f$ | 65 | |

TABLE 7-continued

| | | Starting Compounds | | RT* Protected | RT* Final | Final compounds (I) | |
|---|---|---|---|---|---|---|---|
| | | | | Compounds prepared according to the examples | | | |
| | (III) | (IV) | | | | | |
| X = | Y' = | N° and structure | Method | compound | compound | N° | R = |
| MM | FMOC | 68a | A | 14.1[e] | 24.2–24.6[f] | 68 | |
| MM | FMOC | 72a | A | 9.6[e] | 15.4[f] | 72 | |
| MM | FMOC | 76a | A | 10.2[e] | 16.3[f] | 76 | |
| MM | FMOC | 76a | A | 11.7[e]<br>12.6[e] | 19.8[f]<br>21.8[f] | 80 | |
| MM | FMOC | 81a | A | 12.5[e]<br>14.0[e] | 22.1[f]<br>24.9[f] | 81 | |
| MM | FMOC | 82a | A | 10.9[e] | 19.0[f] | 82 | |

TABLE 7-continued

| | | Starting Compounds | | RT* Protected compound | RT* Final compound | Final compounds (I) | |
|---|---|---|---|---|---|---|---|
| (III) X = | (IV) Y' = | N° and structure | Method | | | N° | R = |
| MM | FMOC | 83a (2-methylphenoxy-CH2-COOH) | A | 10.8[e] | 18.9[f] | 83 | 2-methylphenoxy-CH2- |
| MM | FMOC | 84a (3,5-dimethylphenoxy-CH2-COOH) | A | 11.9[e] | 21.7[f] | 84 | 3,5-dimethylphenoxy-CH2- |
| MM | FMOC | 85a (phenoxy-CH2-CH2-COOH) | A | 10.2[e] | 17.3[f] | 85 | phenoxy-CH2-CH2- |
| MM | FMOC | 86a (PhCH(CH3)CH2COOH) | A | 10.8[e] 11.7[e] | 19.5[f] 20.1[f] | 86 | PhCH(CH3)CH2- |
| MM | FMOC | 87a (PhCH2CH(CH3)COOH) | A | 10.5[e] 11.3[e] | 19.5[f] 21.4[f] | 87 | PhCH2CH(CH3)- |
| MM | FMOC | 88a (2-chlorobenzyl-COOH) | A | 10.8[e] | 17.3[f] | 88 | 2-chlorobenzyl- |
| MM | FMOC | 89a (2-bromobenzyl-COOH) | A | 11.5[e] | 18.0[f] | 89 | 2-bromobenzyl- |

TABLE 7-continued

Compounds prepared according to the examples

| Starting Compounds | | | | RT* | RT* | Final compounds (I) | |
|---|---|---|---|---|---|---|---|
| (III) | (IV) | | | Protected | Final | | |
| X = | Y' = | N° and structure | Method | compound | compound | N° | R = |
| MM | FMOC | 90a (2,6-dichlorobenzyl-COOH) | A | 12.0[e] | 18.8[f] | 90 | 2,6-dichlorobenzyl |
| MM | FMOC | 91a (2-F, 6-Cl benzyl-COOH) | A | 10.5[e] | 17.0[f] | 91 | 2-F, 6-Cl benzyl |
| MM | FMOC | 92a (2,6-difluorobenzyl-COOH) | A | 9.9[e] | 15.5[f] | 92 | 2,6-difluorobenzyl |
| MM | FMOC | 93a (3-fluorobenzyl-COOH) | A | 9.8[e] | 16.0[f] | 93 | 3-fluorobenzyl |
| MM | FMOC | 94a (3-methoxybenzyl-COOH) | A | 9.4[e] | 15.2[f] | 94 | 3-methoxybenzyl |
| MM | FMOC | 95a (3-chlorobenzyl-COOH) | A | 11.0[e] | 18.5[f] | 95 | 3-chlorobenzyl |
| MM | FMOC | 95a (3-bromobenzyl-COOH) | A | 11.7[e] | 19.1[f] | 96 | 3-bromobenzyl |

TABLE 7-continued
Compounds prepared according to the examples
| Starting Compounds | | | | RT* | RT* | Final compounds (I) | |
|---|---|---|---|---|---|---|---|
| (III) | (IV) | | | Protected | Final | | |
| X = | Y' = | N° and structure | Method | compound | compound | N° | R = |
| MM | FMOC | 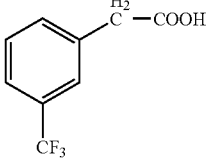 97a | A | 12.2[e] | 21.3[f] | 97 | 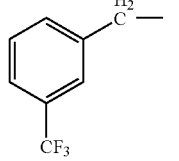 |
| MM | FMOC | 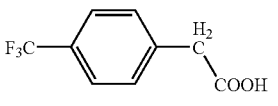 98a | A | 12.0[e] | 21.8[f] | 98 | 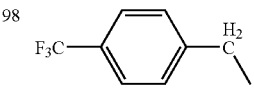 |
| MM | FMOC | 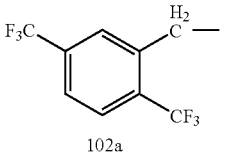 102a | A | 13.6[e] | 24.5[f] | 99 | 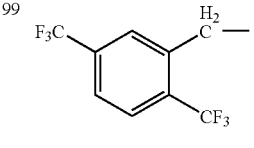 |
| MM | FMOC | 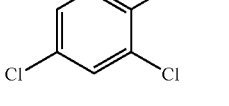 100a | A | 12.4[e] | 21.2[f] | 100 | 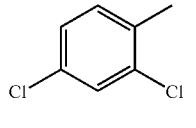 |
| MM | FMOC | 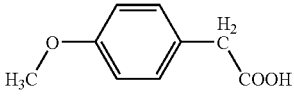 | A | 9.2[e] | 14.4[f] | 101 | 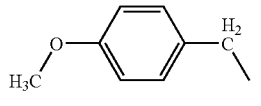 |
| MM | FMOC | 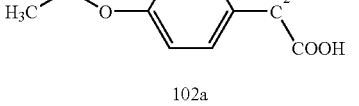 102a | A | 10.4[e] | 17.4[f] | 102 | 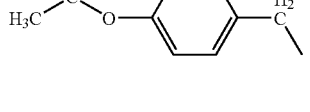 |
| MM | FMOC | 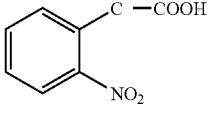 103a | A | 9.3[e] | 13.9[f] | 103 | 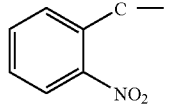 |
| MM | FMOC | 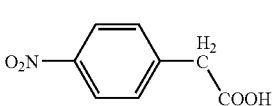 104a | A | 9.7[e] | 14.8[f] | 104 | 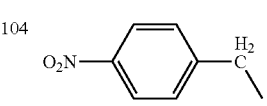 |

TABLE 7-continued

Compounds prepared according to the examples

| Starting Compounds | | | | RT* Protected | RT* Final | Final compounds (I) | |
|---|---|---|---|---|---|---|---|
| (III) X = | (IV) Y' = | N° and structure | Method | compound | compound | N° | R = |
| MM | FMOC | 105a (2-(methylthio)benzoic acid) | A | 9.4[e] | 19.3[f] | 105 | 2-(methylthio)phenyl |
| MM | FMOC | 106a (4-(methylthio)phenylacetic acid) | A | 10.8[e] | 18.1[f] | 106 | 4-(methylthio)benzyl |
| MM | FMOC | 107a (2,5-dimethylphenylacetic acid) | A | 10.8[e] | 20.2[f] | 107 | 2,5-dimethylbenzyl |
| MM | FMOC | 108a (3,5-dimethylphenylacetic acid) | A | 12.0[e] | 21.1[f] | 108 | 3,5-dimethylbenzyl |
| MM | FMOC | 109a (2,4-dimethoxyphenylacetic acid) | A | 10.0[e] | 16.7[f] | 109 | 2,4-dimethoxybenzyl |
| MM | FMOC | 110a (3,4-dimethoxyphenylacetic acid) | A | 8.3[e] | 11.5[f] | 110 | 3,4-dimethoxybenzyl |
| MM | FMOC | 111a (2,3-difluorophenylacetic acid) | A | 10.2[e] | 16.5[f] | 111 | 2,3-difluorobenzyl |

TABLE 7-continued

Compounds prepared according to the examples

| Starting Compounds | | | | RT* Protected compound | RT* Final compound | Final compounds (I) | |
|---|---|---|---|---|---|---|---|
| (III) X = | (IV) Y' = | N° and structure | Method | | | N° | R = |
| MM | FMOC | 112a (3,4-difluorophenyl-CH₂-COOH) | A | 10.6[e] | 17.5[f] | 112 | 3,4-difluorobenzyl |
| MM | FMOC | 113a (2,5-difluorophenyl-CH₂-COOH) | A | 10.3[e] | 16.2[f] | 113 | 2,5-difluorobenzyl |
| MM | FMOC | 114a (3,5-difluorophenyl-CH₂-COOH) | A | 10.6[e] | 17.5[f] | 114 | 3,5-difluorobenzyl |
| MM | FMOC | 115a (4-fluoro-2-chlorophenyl-CH₂-COOH) | A | 10.9[e] | 18.0[f] | 115 | 4-fluoro-2-chlorobenzyl |
| MM | FMOC | 116a (2,3,6-trifluorophenyl-CH₂-COOH) | A | 10.2[e] | 16.0[f] | 116 | 2,3,6-trifluorobenzyl |
| MM | FMOC | 117a ((R)-phenyl-CH(CH₃)-COOH) | A | 10.2[e] | 16.7[f] | 117 | (R)-1-phenylethyl |
| MM | FMOC | 118a ((S)-phenyl-CH(CH₃)-COOH) | A | 10.7[e] | 18.5[f] | 118 | (S)-1-phenylethyl |

TABLE 7-continued

Compounds prepared according to the examples

| Starting Compounds | | | | RT* | RT* | Final compounds (I) | |
|---|---|---|---|---|---|---|---|
| (III) | (IV) | | | Protected | Final | | |
| X = | Y' = | N° and structure | Method | compound | compound | N° | R = |
| MM | FMOC | 119a | A | 11.1[e] | 18.9[f] | 119 | |
| MM | FMOC | 120a | A | 11.1[e] | 17.5[f] | 120 | |
| MM | FMOC | 121a | A | 12.7[e] | 22.5[f] | 121 | |
| MM | FMOC | 122a | A | 10.7[e] | 18.7[f] | 122 | |
| MM | FMOC | 123a | A | 12.3[e] | 20.7/21.1[f] | 123 | |
| MM | FMOC | 124a | A | 14.0[e] | 24.5[f] | 124 | |
| MM | FM0C | 125a | A | 12.9[e] | 20.9[f] | 125 | |

TABLE 7-continued

Compounds prepared according to the examples

| Starting Compounds | | | | RT* Protected compound | RT* Final compound | Final compounds (I) | |
|---|---|---|---|---|---|---|---|
| (III) X = | (IV) Y' = | N° and structure | Method | | | N° | R = |
| MM | FMOC | 126a 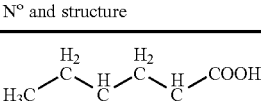 | A | 14.0/14.3[e] | 24.4/25.3[f] | 126 | 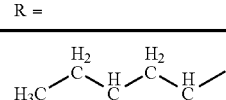 |
| MM | FMOC | 127a 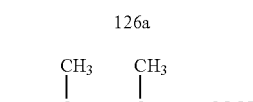 | A | 13.0[e] | 22.6[e] | 127 | 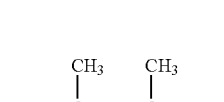 |

*(a) Instrument: Shimadzu SCL-6B; Column: Merck Lichrocart 125-4 Lichrosphere 100 RP-18 (5 μm); Flow. 1 ml/min; detector UV λ = 270; inj.vol. 10 μl; phase A: HCOONH$_4$ 0.05 M, phase B: MeCN; gradient: time 0% B = 35; time 15% B = 40; time 35% B = 70; time 36% B = 85; time 39% B = 85; time 40% B = 35 (b) Instrument: Varian 9010; Column: Merck Lichrocart 125-4 Lichrosphere 100 RP-8 (5 μm); Flow: 1 ml/min; detector UV λ=270; inj.vol. 10 μl; phase A: HCOONH$_4$ 0.05 M, phase B: MeCN; gradient: time 0% B = 30; time 30% B = 40; time 35% B = 80; time 40% B = 80; time 45% B = 30 (c) Instrument: Shimadzu SCL-6B; Column: Merck Lichrocart 125-4 Lichrosphere 100 RP-18 (5 μm); Flow: 1 ml/min; detector UV λ = 270; inj.vol. 10 μl; phase A: HCOONH$_4$ 0.05 M, phase B: MeCN; gradient: time 0% B = 15; time 20% B = 37; time 25% B = 43; time 30% B = 58 (d) Instrument: HP 1090 Column RP-18 (Merck) 5 μm Eluent: Phase A: HCOONH$_4$ 0.05 M Phase B: MeCN Gradient: time 0% B = 35; time 15% B = 40; time 35% B = 70; Flow rate: 1 ml/min; Detection: UV at 270 nm Inj. Vol. 10 μl (e) Instrument: Varian 9010; Column: Merck Lichrocart 125-4 Lichrosphere 100 RP-8 (5 μm); Flow: 1 ml/min: detector UV λ = 270; inj.vol. 10 μl; phase A: HCOONH$_4$ 0.05 M, phase B: MeCN; gradient: time 0% B = 35; time 15% B = 50; time 35% B = 70; time 36% B = 85; time 39% B = 85); time 40% B = 35; time 45% B = 35 (f) Instrument: Varian 1090; Column: Merck Lichrocart 125-4 Lichrosphere 100 RP-8 (5 μm); Flow: 1 ml/min; detector UV λ = 270; inj.vol. 20 μl; phase A: HCOONH$_4$ 0.05 M, phase B: MeCN; gradient: time 0% B = 20; time 30% B = 40; time 35% B = 80; time 40% B = 80; time 45% B = 30; time 50% B = 20 (g) Shimadzu LC-2010A; Column: Merck Lichrocart 125-4 Lichrosphere 100 RP-8 (5 μm); Flow: 1 ml/min; detector UV λ = 254; inj.vol. 10 μl; phase A: HCOONH$_4$ 0.05 M, phase B: MeCN; gradient: time 0% B = 5; time 20% B = 30; time 30% B = 50; time 40% B = 70; n.a. not available.

The $^1$H-NMR data of compounds 10, 13, 14, 23, 24, 37, 39 and 49 are reported in TABLE 8. The molecular weights of compounds described in the examples determined through MS spectometry are reported in TABLE 9.

TABLE 8

$^1$H chemical shifts in ppm: NMR measurements were carried out on a Bruker DRX 500 spectrometer operating at 500.13 MHz. Samples containing 5 mM of ramoplanin derivative in D$_2$O-DMSO-d$_6$ (4:1) were utilised. For identification and assignment of the spin system two-dimensional $^1$H-COSY and TOCSY spectra were recorded at 313 K.

| Residue | | COMPOUND N° | | | | | | | |
|---|---|---|---|---|---|---|---|---|---|
| | | 49 | 23 | 24 | 37 | 39 | 13 | 14 | 10 |
| Side chain | | 3.55(2H) | 5.826(2H) | 5.84(1H) | 0.98(3H) | 3.52(2H) | 3.99(2H) | 3.55(2H) | 1.37(3H) |
| | | 2.19(6H) | 6.67(1H) | 6.7(1H) | 5.56(1H) | 2.17(3H) | 7.95(1H) | 7.3(2H) | 4.13(2H) |
| | | 7.03(2H) | 2.12(2H) | 2.19(2H) | 6.49(1H) | 7.1(1H) | 7.91(1H) | 7.35(3H) | 7.57(2H) |
| | | 7.13(2H) | 1.35(2H) | 1.39(2H) | 7.07(1H) | 7.7(1H) | 7.87(1H) | | 6.98(2H) |
| | | | 0.843(3H) | 1.2–1.29(4H) | 6.17(1H) | 7.18(1H) | 7.57(1H) | | |
| | | | | 0.84(3H) | 2.14(2H) | 7.21(1H) | 7.56(1H) | | |
| | | | | | | | 7.47(1H) | | |
| | | | | | | | 7.39(3H) | | |
| Asn (1)[1] | CHα | 4.75 | 4.72 | 4.72 | 4.7 | 4.55 | 4.55 | 4.7 | 4.71 |
| | CH$_2$β | 1.6–2.2 | 1.8–2.24 | 1.82–2.33 | 1.66–2.18 | 1.68–2.18 | 1.83–2.24 | 1.79–2.21 | 1.88–1.22 |
| Leu (15) | CHα | 4.13 | 4.14 | 4.153 | 4.285 | 4.07 | 3.95 | 4.06 | 4.18 |
| | CH$_2$β | 1.46 | 1.54 | 1.5 | 1.503 | 1.39 | 1.16–1.22 | 1.42–1.46 | 1.4–1.44 |
| | CHγ | 1.46 | 1.54 | 1.5 | 1.503 | 1.45 | 1.33 | 1.44 | 1.4 |
| | Me | 0.72–0.79 | 0.76 | 0.766 | 0.765–0.8 | 0.67–0.76 | 0.43–0.56 | 0.62–0.74 | 0.68 |
| Ala (16) | CHα | 4.18 | 4.35 | 4.36 | 4.36 | 4.195 | 4.097 | 4.25 | 4.34 |
| | Me | 1.14 | 1.44 | 1.45 | 1.428 | 1.178 | 0.93 | 1.244 | 1.46 |

[1]Aminoacid residues are numerated accordingly to R. Ciabatti et al. J. Antibiot. (1989) 42, pag. 254–267

TABLE 9

| Compound N° | Lower Isotope Molecular Weight |
|---|---|
| MS spectrometry data[1] | |
| 1 | 2552 |
| 2 | 2500 |
| 3 | 2514 |
| 4 | 2528 |
| 5 | 2542 |
| 6 | 2556 |
| 7 | 2570 |
| 8 | 2520 |
| 9 | 2534 |
| 10 | 2564 |
| 11 | 2545 |
| 12 | 2596 |
| 13 | 2584 |
| 14 | 2534 |
| 15 | 2548 |
| 16 | 2552 |
| 17 | 2568 |
| 18 | 2613 |
| 19 | 2548 |
| 20 | 2550 |
| 21 | 2562 |
| 22 | 2592 |
| 23 | 2512 |
| 24 | 2540 |
| 25 | 2510 |
| 26 | 2534 |
| 27 | 2570 |
| 28 | 2570 |
| 29 | 2584 |
| 30 | 2610 |
| 31 | 2514 |
| 32 | 2524 |
| 33 | 2552 |
| 34 | 2538 |
| 35 | 2538 |
| 36 | 2538 |
| 37 | 2524 |
| 38 | 2534 |
| 39 | 2548 |
| 40 | 2542 |
| MS spectrometry data[2] | |
| 43 | 2224 |
| 47 | 2562 |
| 49 | 2562 |
| 50 | 2548 |
| 54 | 2546 |
| 55 | 2578 |
| 56 | 2602 |
| 57 | 2564 |
| 63 | 2543 |
| 65 | 2543 |
| 68 | 2557 |
| 72 | 2552 |
| 76 | 2570 |
| 80 | 2576 |
| 81 | 2590 |
| 82 | 2562 |
| 83 | 2550 |
| 84 | 2578 |
| 85 | 2564 |
| 86 | 2562 |
| 87 | 2562 |
| 88 | 2568 |
| 89 | 2613 |
| 90 | 2602 |
| 91 | 2586 |
| 112 | 2570 |
| 113 | 2570 |
| 114 | 2570 |
| 115 | 2586 |
| 116 | 2588 |
| 117 | 2548 |
| 118 | 2548 |
| 119 | 2526 |
| 120 | 2540 |
| 121 | 2540 |
| 122 | 2528 |
| 123 | 2542 |
| 124 | 2556 |
| 125 | 2542 |
| 126 | 2556 |
| 127 | 2542 |

[1]Instrument: Finnigan LCQ Deca. Compounds were dissolved in H$_2$O (with 0.1% of trifluoroacetic acid):MeCN 1:1 and detected by flow-injection.
[2]Instrument: Finnigan LCQ Deca. Compounds were dissolved in H$_2$O (with 0.1% of trifluoroacetic acid):MeCN 1:1 and detected by flow-injection.

Preparation of the Starting 4,10-Protected RAMO-NH$_2$ (III)

Preparation of 4,10 DIFMOC Protected RAMO-NH$_2$

Step I: Protection of the Ornitine Moieties of Ramoplanin

A solution of ramoplanin dihydrochloride having 95% (w/w) title (110.6 g, 40 mmol) in dimethylformamide (500 ml) was maintained at 0° C. with stirring under nitrogen atmosphere. To this solution N-(9-fluorenylmethoxycarbonyloxy)-succinimide (FMOC-ONSu) (6.8 g, 20 mmol) and TEA (5.8 ml, 41.2 mmol) were added maintaining the reaction at 0–5° C. After 5 minutes further FMOC-ONSu (6.8 g, 20 mmol) and TEA (5.8 ml, 41.2 mmol) were added. After other 5 minutes, FMOC-ONSu (13.6 g, 40 mmol) was added. The reaction'temperature was allowed to rise at room temperature. Reaction was monitored by HPLC analysis (Retention time 25.6 minutes. Instrument: Shimadzu SCL-6B; Column: Merck Lichrocart 125-4—Lichrosphere 100 RP-18 (5 µm); Flow: 1 ml/min; detector UV λ=270; inj. Vol. 10 µl; phase A: HCOONH$_4$ 0.05M, phase B: MeCN; gradient: time 0% B=35; time 15% B=40; time 35% B=70). After HPLC control additional 10.8 g of FMOC-ONSu were necessary to complete the reaction. After 30 minutes acetic acid (20 ml) was added and the reaction mixture was poured in ethyl acetate (6 l). The precipitated was filtered, washed with ethyl acetate (1 l) and dried. 133 grams of a solid product were obtained. The solid was washed under stirring in methanol/water (1:9) adjusted at pH 4.5–5 with acetic acid. The solid was filtered and dried at 35° C. under reduced pressure obtaining 126.8 grams of white solid. Yield 100%. MS: Lower Isotope Molecular Weight=2996.

Step II: Reductive Ozonolysis

Synthesis of 4,10-diFMOC Protected RAMO-NHCO-CHO

To a solution of 4,10-diFMOC protected RAMO-NH$_2$ obtained in the previous step (30 g) in methanol/DMF (9:1, 800 ml), cooled at −78° c., ozone was bubbled (40 mmol, at a flow rate of 100 l/hour of oxygen containing 5% of ozone) under stirring. The reaction was maintained at −78° C. for 30 minutes. The reaction was monitored by HPLC analysis (Retention time 7.5 minutes. Instrument and condition as above). The excess of ozone was eliminated by bubbling nitrogen into the solution. Triphenylphosphine was added (5.8 g) and the reaction was allowed to reach the room temperature. Methanol was evaporated under reduced pressure and the residual DMF solution was poured in ethyl acetate (2 l) under stirring. The precipitated was filtered, washed with ethyl acetate (3×150 ml) dried at room temperature, obtaining 31.5 grams of a solid. Yield 100%. MS: Lower Isotope Molecular Weight=2916.

Step III: Reductive Amination

Synthesis of 4,10-diFMOC Protected RAMO-NHCOCH$_2$NHCH$_2$C$_6$H$_5$

To a solution of 4,10-diFMOC protected RAMO-NHCO-CHO (110 g, 38 mmol) and benzylamine hydrobromide (36.5 g, 194 mmol) in anhydrous DMF (925 ml) NaCNBH$_3$ (3.58 g, 57 mmol) was added under stirring at room temperature. The mixture was stirred for 2 hours. The reaction was monitored by HPLC analysis (Retention time 19.6 minutes. Instrument and conditions as above). The solution was poured into water (9 L). The precipitate was filtered and dried at 35° C. under reduced pressure obtaining 107 g of crude product.

Purification:

The crude product (107 g) was dissolved at 35° C.–40° C. in 1.5 L of (1:1) acetonitrile:water mixture at pH 2.5 (HCl 1N). To this solution, under stirring, silanized silica gel was added (300 g). After 30 minutes acetonitrile was evaporated under reduced pressure and the water suspension was charged at the top of a silanized silica gel column (diameter 7.5 cm, height 100 cm) previously stabilized with water. The elution was carried on with water:acetonitrile gradient starting from 85:15 to 1:1. Fractions containing the products were collected and the acetonitrile was evaporated under reduced pressure. The precipitate was filtered, washed with water (100 ml), dried at 35° C. under reduced pressure obtaining 20.6 grams of white solid. Yield 18% (from ramoplanin). MS: Lower Isotope Molecular Weight=3007.

Step IV: Edman Degradation

Synthesis of 4,10-diFMOC Protected RAMO-NH$_2$

To a solution of 4,10-diFMOC protected RAMO-NHCOCH$_2$NHCH$_2$C$_6$H$_5$ (17 g, 5.65 mmol) in pyridine:water 1:1 (340 ml), phenylisothiocyanate (0.76 ml, 6.35 mmol) was added while stirring at room temperature. The reaction was monitored by HPLC analysis (Retention time 24.7 minutes. Instrument and conditions as above). After 1 hour the solvent was evaporated and the residue was suspended in toluene (50 ml) and evaporated. This operation was repeated twice. The solid was then suspended in dichloromethane (100 ml) and added with TFA (100 ml). After 15 minutes at 40° C. and HPLC control (Retention time 9.5 minutes. Instrument and conditions as above) the mixture was evaporated under reduced pressure and the obtained oil was triturated with diethyl ether (300 ml). The solid product was filtered, washed with diethyl ether (100 ml), dried at 35–40° C. under reduced pressure obtaining 17 grams of solid. The solid was suspended in water, the suspension was stirred at room temperature for 2 hours and filtered; the solid was dried at 35–40° C. under reduced pressure, obtaining 15 grams of white solid. MS: Lower Isotope Molecular Weight=2860.

Preparation of 4,10-diCBZ Protected RAMO-NH$_2$

Step I: Protection of the Ornitine Moieties of Ramoplanin

A solution of ramoplanin dihydrochloride having 95% title (w/w) (40 mmol) in dimethylformamide (500 ml) was maintained at 0° C. with stirring under nitrogen atmosphere. To this solution dibenzyldicarbonate (80 mmol) and TEA (80 mmol) were added maintaining the reaction at 0–5° C. The reaction was allowed to rise to room temperature. The reaction was monitored by HPLC analysis (Retention time 16.0 minutes. Instrument and conditions as above). After 1 hours the reaction was poured in ethyl acetate (6 l) and the precipitate was filtered, washed with diethyl ether (1 l), dried at 35–40° C. under reduced pressure obtaining 125 grams of white solid. Yield 100%. MS: Lower Isotope Molecular Weight=2820.

Step II: Reductive Ozonolysis

Synthesis of 4,10-diCBZ Protected RAMO-NHCOCHO

The same procedure used for the corresponding FMOC protected compound was followed. The reaction was monitored by HPLC analysis (Retention time 10.0 minutes. Instrument and conditions as above). Yield 100%. MS: Lower Isotope Molecular Weight=2740.

Step III: Reductive Amination

Synthesis of 4,10-diCBZ Protected RAMO-NHCOCH$_2$NHCH$_2$C$_6$H$_6$

The same procedure used for the corresponding FMOC protected compound was followed. The reaction was monitored by HPLC analysis (Retention time 13.8 minutes. Instrument and conditions as above). MS: Lower Isotope Molecular Weight=2831.

Step IV: Edman degradation

Synthesis of 4,10-diCBZ protected RAMO-NH$_2$

The same procedure used for the corresponding FMOC protected compound was followed. The reaction was monitored by HPLC analysis (Retention time 11.0 minutes). Instrument and conditions as above). MS: Lower Isotope Molecular Weight=2684.

Preparation of Carboxylic Acids Starting Material of Formula (IV):

Many carboxylic acids starting materials of formula (IV) employed according to TABLE 7 are commercially available products. The carboxylic acids which are not commercially available were prepared according to the following procedures.

Compound 1a: 2Z,4E-7-Methyl-octa-2,4-dienoic Acid

Step 1: Sodium hydride, as a 60% mineral oil dispersion, (6.8 g, 169 mmol) was introduced into a dry round bottomed flask, and dry tetrahydrofuran (220 ml) was added thereto. The flask was stoppered with a serum cap, cooled in ice and flushed with nitrogen. Ethyl acetoacetate (20 g, 154 mmol) was added dropwise to the cooled and stirred slurry and the reaction was stirred for 10 minutes after the addition was complete. The solution was cooled at −78° C. and a solution of n-butyl lithium (85 ml of 2M solution in cyclohexane) was added dropwise to the reaction mixture and stirring was continued for a further 10 minutes. 3-Methylbutyraldehyde (154 mmol) was then added in one portion. After a further 10 minutes the reaction was poured in a HCl solution (50 ml of 37% HCl in 400 of water). Diethyl ether was added; the aqueous layer was removed and extracted again with 2×40 ml of diethyl ether. The ethereal extracts were combined, washed with a saturated brine solution, dried over sodium sulfate, filtered, and the solvent removed under reduced pressure. The oily residue was purified by flash chromatography using hexane:ethyl acetate=8:2 as eluent obtaining 16.6 g of 5-hydroxy-7-methyl-3-oxo-octanoic acid ethyl ester. Yield 50%.

$^1$H-NMR: (CDCl$_3$, 500 MHZ): chemical shift, p.p.m. 0.95 (d, 6H, Me$_2$—CH); 1.19 (m, 1H, CH$_2$-iPr); 1.28 (t, 3H, CH$_2$CH$_3$); 1.51 (m, 1H, CH$_2$-iPr); 1.80 (m, 1H, CHMe$_2$); 2.65 (dd, 1H, HOCHCH$_2$CO); 2.68 (s broad, 1H, OH); 2.73 (dd, 1H, HOCHCH$_2$CO); 3.47 (s, 2H, COCH$_2$COOEt); 4.16 (m, 1H, HOCHCH$_2$CO); 4.21 (q, 2H, CH$_2$CH$_3$).

Step 2: Sodium borohydride (1.58 g, 41.6 mmol) was added to a stirred solution of the product obtained according to Step 1 (41.6 mmol) in methanol (100 ml) at −30° C. Stirring was continued at the same temperature for 2 hours. Then a saturated ammonium chloride solution was added and methanol was evaporated under reduced pressure. The mixture was extracted with ethyl acetate; the organic layer was dried over sodium sulfate and concentrated to give the 3,5-dihydroxy-7-methyl-octanoic acid ethyl ester intermediate, which was used without any further purification for the following step.

Step 3: Toluene (100 ml) and paratoluene sulfonic acid (800 mg) were added to the product of Step 2 and the mixture was refluxed for 2 hours. The reaction was quenched with water and extracted with ethyl acetate. The organic layer was dried over sodium sulfate and evaporated to give 6 g of the lactone of 7-methyl-5-hydroxy-oct-2-enoic-acid which was used as such for the following step.

$^1$H-NMR: (CDCl$_3$, 500 MHZ) chemical shift p.p.m. 0.97 (d, 6H, M$\underline{e}_2$—CH); 1.41 (m, 1H, C$\underline{H}_2$-iPr); 1.80 (m, 1H, C$\underline{H}_2$-iPr); 1.92 (m, 1H, C$\underline{H}$Me$_2$); 2.31 (m, 2H, C$\underline{H}_2$CH=CH); 4.52 (m, 1H, C$\underline{H}$OCO); 6.04 (m, 1H, CH=C$\underline{H}$COO); 6.90 (m, 1H, C$\underline{H}$=CHCOO).

Step 4: A mixture of the lactone obtained according to Step 3 (38.9 mmol) and tetrabutylammonium fluoride (38.9 mmol) in tetrahydrofuran (100 ml) was stirred at room temperature for 3 hours under nitrogen. Water was added and the mixture was extracted with ethyl acetate. The organic layer was washed with saturated brine solution, dried over sodium sulfate and evaporated under reduced pressure to give 3.8 g of the dienoic acid 1a of the title. Yield 60% from the intermediate product obtained according to Step 1. The dienoic acid was purified by flash chromatography (CHCl$_3$:MeOH=95:5).

Compound 1a: $^1$H-NMR (CDCl$_3$, 500 MHZ): chemical shift p.p.m. 0.93 (d, 6H, M$\underline{e}_2$—CH); 1.73 (m, 1H; C$\underline{H}$Me$_2$); 2.11 (m con J=7.4 Hz, 2H, C$\underline{H}_2$CH=CH); 5.6 (d con J=11.4 Hz, 1H, C$\underline{H}$COOH); 6.12 (dt con J=15.2 e 7.4, 1H, C$\underline{H}$CH$_2$); 6.66 (dd con J$_1$=J$_2$=11.3, 1H, C$\underline{H}$=CHCOOH); 7.33 (m con J=15.2 Hz, 1H, C$\underline{H}$=CHCH$_2$). $^{13}$C-NMR (CDCl$_3$, 500 MHZ): chemical shift p.p.m. 170.6, 147.0, 145.3, 127.4, 113.9, 41.7, 29.1, 22.2.

Following the same procedure, but changing the starting aldehyde, compounds 35a, 36a and 37a were synthesised.

Compound 35a: $^1$H-NMR (CDCl$_3$, 500 MHZ): chemical shift p.p.m. 0.98 (t, 3H); 1.45 (m, 2H); 2.17 (m, 2H); 5.58 (d, 1H, J=11.33 Hz); 6.12 (m, 1H, J=15.2 Hz); 6.65 (dd, 1H); 7.34 (m, 1H).

Compound 36a: $^1$H-NMR (CDCl$_3$, 500 MHZ): chemical shift p.p.m. 1.05 (d, 6H); 2.48 (m, 1H); 5.6 (d, 1H, J=11.31 Hz); 6.08 (m, 1H); 6.65 (dd, 1H); 7.3 (m, 1H).

Compound 37a: $^1$H-NMR (CDCl$_3$, 500 MHZ): chemical shift p.p.m. 1.07 (t, 3H); 2.25 (m, 2H); 5.59 (d, 1H, J=11.35 Hz); 6.17 (m, 1H); 6.66 (dd, 1H); 7.35 (m, 1H).

Compound. 33a: (2E,4E)-7-Methyl-octa-2,4-dienoic Acid

Compound 33a, trans-trans isomer of compound 1a, was synthesised following the same synthetic strategy of compound 1a but changing the final step.

Step 4: A mixture of the lactone obtained according to the above Step 3 (2.143 mmol) and NaOH 30% (11 ml) was stirred at reflux for 1 hours. The mixture was acidified with HCl 5M until pH 3 and then extracted with ethyl acetate. The organic layer was washed with saturated brine solution, dried over sodium sulphate and evaporated under reduced pressure to give a crude product which was purified by flash chromatography (chloroform:methanol=9:1). 0.37 g of desired title compound were obtained. Yield=60%.

Compound 33a: $^1$H-NMR (CDCl$_3$, 500 MHZ): chemical shift p.p.m. 0.9 (d, 6H, M$\underline{e}_2$—CH); 1.76 (m, 1H; C$\underline{H}$Me$_2$); 2.1 (t, 2H, C$\underline{H}_2$CH=CH); 5.82 (d, 1H, J=15.36 Hz, C$\underline{H}$COOH); 6.12–6.3 (m, 2H); 7.29 (m, 1H).

Following the same procedure, changing the starting aldehyde, compounds 32a and 34a were synthesised.

Compound 32a: $^1$H-NMR (CDCl$_3$, 500 MHZ): chemcial shift p.p.m. 0.93 (t, 3H); 1.45 (m, 2H); 2.17 (m, 2H); 5.77 (d, 1H, J=15.31 Hz); 6.15–6.3 (m, 2H); 7.25 (m, 1H).

Compound 34a: $^1$H-NMR (CDCl$_3$, 500 MHZ): chemical shift p.p.m. 1.07 (d, 6H); 2.43 (m, 1H); 5.8 (d, 1H J=15.24 Hz); 6.15 (m, 1H); 6.24 (m, 1H); 7.26 (m, 1H).

Compound 22a: 4-Butoxy-benzoic Acid

Step 1: A mixture of 4-hydroxy-benzaldheide (8.2 mmol), butyl bromide (8.2 mmol), K$_2$CO$_3$ (8.2 mmol) and KI (8.2 mmol) in acetone (15 ml) was stirred at reflux for 6 h. Acetone was evaporated and the semisolid residue was dissolved in water and extracted with ethyl acetate. The organic layer was washed with NaOH 0.1N and then with a saturated brine solution, dried over sodium sulfate and evaporated under reduced pressure to give a crude product which was used as such for the following step. Yield 100%

Step 2: AgNO$_3$ solution (4.6 M in water, 0.56 ml) was added to the solution of the compound obtained according to Step 1 (1.12 mmol) in ethanol (6.7 ml). KOH (5.6 ml of a 1M solution in water) was added and the reaction mixture was stirred at room temperature for 2 hours. The solid was filtered and the aqueous solution was acidified to pH 1 with concentrated hydrochloric acid and extracted with diethyl ether. The organic phase was washed with water, dried over sodium sulphate and evaporated under reduced pressure to give the desired acid (22a) of the title which was used without any further purification for the amidation step.

Compound 22a: $^1$H-NMR (DMSO-d$_6$, 500 MHZ): chemical shift p.p.m. 0.92 (t, 3H); 1.43 (m, 2H); 1.7 (m, 2H); 4.03 (t, 2H); 7.00 (d, 2H); 7.86 (d, 2H).

Compound 40a: 2-Ethyl-hexanoic Acid

To a solution of 2-ethyl hexanol (8.7 mmol) in CH$_2$Cl$_2$ (10 ml), RuCl$_3$H$_2$O (0.014 mmol) and tetra butyl ammonium bromide (0.2 mmol) were added. The mixture was heated at 40° C. and 30% H$_2$O$_2$ (v/v) (3 ml) was added dropwise. After 1 hours the reaction was complete. Water is added, the organic phase was separated, dried over sodium sulphate and evaporated under reduced pressure to give the crude product of the title that was purified by flash chromatography (pure CH$_2$Cl$_2$) obtaining 0.8 g of the desired product. Yield 65%.

Compound 40a: $^1$H-NMR (CDCl$_3$, 500 MHZ): chemical shift p.p.m. 0.92 (m, 6H); 1.3 (m, 4H); 1.45–1.75 (m, 4H); 2.29 (m, 1H); 10.4 (broad, 1H).

Compund 82a: 2-Ethyl phenylacetic Acid

Step 1: Sodium hydride, as a 60% mineral oil dispersion (240 mg, 6 mmol) was introduced into a dry round bottomed flask and dry N,N-dimethylformamide (12 ml) was added thereto. The flask was stoppered with a serum cap and flushed with argon. A solution of ethyl cyanoacetate (679 mg, 6 mmol) in N,N-dimethylformamide (3 ml) was added dropwise to the stirred slurry and the reaction was stirred for 10 minutes after the addition was complete. 2-Ethyl iodobenzene was then added in one portion, followed by copper (I) iodide (1143 mg, 6 mmol). The mixture was heated at 95° C. for 4 h, then cooled to 0° C. and poured into 1 N hydrochloric acid (100 ml). Diethyl ether was added; the aqueous layer was removed and extracted again with 3×100 ml of diethyl ether. The ethereal extracts were combined, dried over sodium sulfate, filtered and the solvent was removed under reduced pressure. The oily residue was purified by flash chromatography using hexane:ethyl acetate: dichlorometane 8:1:1 as eluent, obtaining 326 mg of ethyl cyano(2-ethylphenyl) acetic acid ethyl ester as a colourless oil. Yield 50%.

$^1$H-NMR: (CDCl$_3$, 500 MHz) chemical shift p.p.m. 1.25 (t, 3H, ArCH$_2$C$\underline{H}_3$); 1.27 (t, 3H, COOCH$_2$C$\underline{H}_3$); 2.72 (m, 2H, ArC$\underline{H}_2$CH$_3$); 4.24 (m, 2H, COOC$\underline{H}_2$CH$_3$); 4.92 (s, 1H, NCC$\underline{H}$COOEt); 7.26 (m, 2H, ArH$\underline{}$); 7.34 (m, 1H, ArH$\underline{}$); 7.47 (m, 1H, ArH$\underline{}$).

Step 2: A mixture of the cyano(2-ethylphenyl) acetic acid ethyl ester obtained according to the above step 1 (1.5 mmol) and 1 N sodium hydroxide (10 ml) was stirred at reflux for 40 h. The mixture was acidified with concentrated hydrochloric acid until pH 2 and then extracted with 2×20 ml of ethyl acetate. The organic extracts were combined, washed with saturated brine solution, dried over sodium sulphate and evaporated under reduced pressure to give 222 mg of desired title compound as a white solid. Yield 90%.

Compound 82a: $^1$H-NMR: (CDCl$_3$, 500 MHz) chemical shift p.p.m. 1.23 (t, 3H, ArCH$_2$C$\underline{H}_3$); 2.68 (q, 2H, ArC$\underline{H}_2$CH$_3$); 3.70 (s, 2H, C$\underline{H}_2$COOH); 7.17 (m, 1H, ArH$\underline{}$); 7.24 (m, 3H, ArH$\underline{}$).

Compound 49a: Following the same procedure, but using 2,6-dimethyliodobenzene instead of 2-ethyliodobenzene, compound 49a was synthesized.

$^1$H-NMR: (CDCl$_3$, 500 MHz) chemical shift p.p.m. 2.35 (s, 6H, ArCH$_3$); 3.74 (s, 2H, CH$_2$COOH); 7.04. (m, 2H, ArH); 7.08 (m, 1H, ArH).

Compound 122a: 3-ethyl-pentanoic Acid

Step 1: Dry tetrahydrofuran (20 ml) was introduced into a dry round bottomed flask and sodium hydride (1.3 g 32.67 mmoli), as a 60% mineral oil dispersion, was added thereto. The flask was cooled at 0° C. and flushed with argon. Methyl diethyl-phosphono acetate (5 ml 27.23 mmoli) was added dropwise to the cooled and stirred slurry. The reaction solution was stirred for 15 minutes, and then diethyl ketone (2.9 ml 27.23 mmoli) was added and the temperature was left to raise at room temperature. The reaction was stirred overnight under argon atmosphere. Dichloromethane (100 ml) was added and the organic phase was washed with 1N hydrochloric acid (100 ml) and water (100 ml). The organic phase was separated and dried over sodium sulfate, filtered, and then the solvent was removed under reduced pressure.

The oily residue was purified by flash chromatography (Instrument: CombiFlash Sq 16× by Isco Column: Redi Sep Method: Phase A n-hexane; Phase B ethylacetate Detector UV=230 nm; flow 40 ml/min T=0% B=0, T=20% B=10, T=30% B=20) obtaining 3.28 g of 3-ethyl-pent-2-enoic acid methyl ester as colourless oil. Yield 84.8%

$^1$H-NMR: (CDCl$_3$, 600 MHz) chemical shift p.p.m. 1.05–1.09 (m, 6H, CH$_2$CH$_3$); 2.20 (q, 2H, CH$_3$CH$_2$); 2.63 (q, 2H, CH $_3$CH$_2$); 5.61 (s, 1H, CCHC(O)).

Step 2: 3-ethyl-pent-2-enoic acid methyl ester (150 mg, 1.056 mmol) was dissolved in dioxane (1 ml), and palladium 10% on activated carbon (30 mg) was added; the slurry was hydrogenated under pressure (40 p.s.i.) for 4 h. The carbon was filtered off and the filter was washed with dioxane (1 ml); 1N NaOH (2 ml) was added to the mixture which was left overnight at room temperature; after addition of 1N hydrochloric acid (3 ml), the product was extracted with ethyl acetate. The organic solution was dried over sodium sulfate, filtered and the solvent was removed under reduced pressure, obtaining 90 mg of 3-ethyl pentanoic acid as colourless oil. Yield 65.5%.

Compound 122a: $^1$H-NMR: (CDCl$_3$, 500 MHz) chemical shift p.p.m. 0.90 (t, 6H, CH$_2$CH$_3$); 1.35–1.43 (m, 4H, CH$_3$CH$_2$); 1.75–1.78 (m, 1H, CH$_2$CH); 2.29 (d, 2H, CH$_2$C(O)).

Following the same procedure, but using the appropriate carbonyl derivative (aldehyde or ketone) and methyl diethyl phosphono derivative (acetate or 2 propionate) as the starting material, the following compounds were synthesized.

Compound 63a: $^1$H-NMR: (CDCl$_3$, 500 MHz) chemical shift p.p.m. 0.88–0.92 (m, 6H, CH$_2$CH$_3$); 1.25–1.42 (m, 6H, CH$_3$CH$_2$CH$_2$, CH$_3$CH$_2$); 1.82–1.84 (m, 1H, CH$_2$CH); 2.28 (d, 2H, CH$_2$C(O)).

Compound 65a: $^1$H-NMR: (CDCl$_3$, 500 MHz) chemical shift p.p.m. 0.86 (t, 6H, CH$_2$CH$_3$); 1.22–1.25 (m, 1H, CH$_2$CH); 1.28–1.34 (m, 4H, CH$_3$CH$_2$); 1.59–1.64 (m, 2H, CH CH$_2$); 2.32–2.35 (m, 2H, CH$_2$C(O)).

Compound 68a: $^1$H-NMR: (CDCl$_3$, 500 MHz) chemical shift p.p.m. 0.85–0.95 (m, 9H, CHCH$_3$); 1.09 (d, 1.5H, CH CH$_3$); 1.15 (d, 1.5H, CHCH$_3$) diastereomers; 1.05–1.23 (m, 2H, CHCH$_2$); 1.6–1.67 (m, 1H, CH$_3$CH); 1.85–1.87 (m, 0.5H, CH$_3$CH); 1.98–2.00 (m, 0.5H, CH$_3$CH) diastereomers; 2.38–2.43 (m, 1H, CH$_3$CH).

Compound 123a: $^1$H-NMR: (CDCl$_3$, 500 MHz) chemical shift p.p.m. 0.84–0.92 (m, 6H, CH$_2$CH$_3$); 1.09 (d, 3H, CH CH$_3$); 1.30–1.33 (m, 2H, CH$_3$CH$_2$); 1.34–1.42 (m, 2H, CH$_3$CH$_2$); 1.60–1.62 (m, 1H, CH$_3$CH); 2.55–2.58 (m, 1H, CHCH).

Compound 124a: $^1$H-NMR: (CDCl$_3$, 500 MHz) chemical shift p.p.m. 0.86–0.93 (m, 6H, CH$_2$CH$_3$); 1.09 (d, 1.5H, CHCH$_3$); 1.10 (d, 1.5H, CHCH$_3$) diastereomers; 1.28–1.36 (m, 4H, CH$_3$CH$_2$); 1.37–1.46 (m, 2H, CHCH$_2$); 1.69–1.71 (m, 1H, CH$_2$CH); 2.55–2.59 (m, 1H, CHC(O)).

Compound 126a: $^1$H-NMR: (CDCl$_3$, 500 MHz) chemical shift p.p.m. 0.83–0.86 (m, 6H, CH$_2$CH$_3$); 1.18 (d, 3H, CH CH$_3$); 1.25–1.35 (m, 6H, CHCH$_2$); 1.64–1.69 (m, 1H, CH$_2$ CH); 2.52–2.56 (m, 1H, CHC(O)).

Compound 127a: $^1$H-NMR: (CDCl$_3$, 500 MHz) chemical shift p.p.m. 0.87–0.90 (m, 6H, CHCH$_3$); 0.96 (d, 3H, CH CH$_3$); 1.08–1.19 (m, 2H, CHCH$_2$); 1.62–1.66 (m, 1H, CH$_3$ CHCH$_3$); 2.04–2.07 (m, 1H, CH$_2$CHCH$_3$); 1.14 (dd, 1H, CH$_2$C(O)); 2.34 (dd, 1H, CH$_2$C(O)).

Compound 119a: 3-Ethyl pent-2-enoic acid The acid 119a was obtained following the same synthesis of compound 122a but changing the second step.

Step 2: 3-ethyl pent-2-enoic acid methyl ester (200 mg, 1.4 mmol) was dissolved in dioxane (1 ml). 1N NaOH (1 ml) was added, and the mixture was left overnight at 50° C.; 1N hydrochloric acid was added (2 ml), and the compound was extracted with ethyl acetate. The organic solution was dried over sodium sulfate, filtered and the solvent was removed under reduced pressure, obtaining 162 mg of 3-ethylpent-2-enoic acid as colourless oil. Yield 90%. $^1$H-NMR: (CDCl$_3$, 500 MHz) chemical shift p.p.m. 1.06–1.11 (m, 6H, CH$_2$ CH$_3$); 2.23 (q, 2H, CH$_3$CH$_2$); 2.64 (q, 2H, CH$_3$CH$_2$); 5.65 (s, 1H, CHC(O)).

According to the same procedure the following compounds were synthesized using the corresponding methyl esters (prepared according to the first step described for the preparation of compound 122a) as the starting material:

Compound 120a: $^1$H-NMR: (CDCl$_3$, 500 MHz) chemical shift p.p.m. 1.01–1.09 (m, 6H, CH$_2$CH$_3$); 1.91 (s, 1H, CCH$_3$); 2.20 (q, 2H, CH$_3$CH$_2$); 2.46 (q, 2H, CH$_3$CH$_2$).

Compound 121a: $^1$H-NMR: (CDCl$_3$, 500 MHz) chemical shift p.p.m. 0.85–0.89 (m, 6 h, CH$_2$CH$_3$); 1.35–1.41 (m, 2H, CH$_2$CH$_3$); 1.48–1.55 (m, 2H, CH$_2$CH$_3$); 2.02–2.05 (m, 1H, CH$_2$CH); 5.81 (d, 1H, CHCH); 6.86 (q, 1H, CHC(O)).

The invention claimed is:

1. A ramoplanin derivative of the following formula

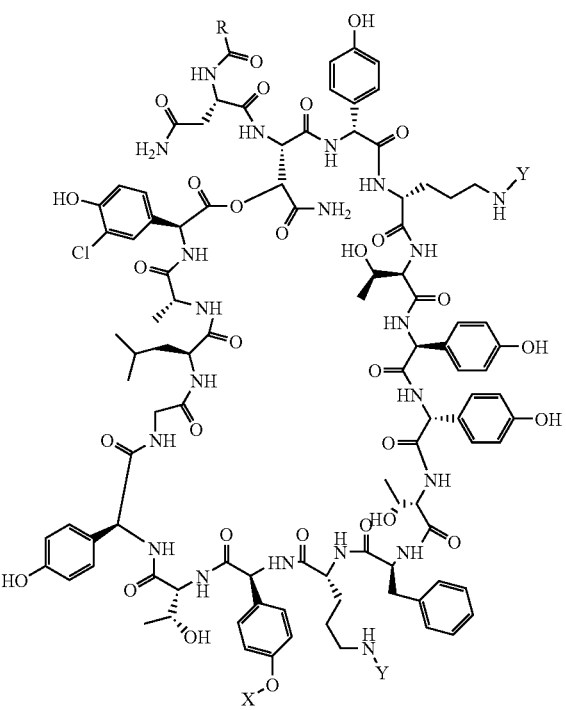

wherein X is selected from the group consisting of hydrogen, 2-α-D-mannopyranosyl, 2-O-α-D-mannopyranosyl-α-D-mannopyranosyl, and 2,3-O-di[α-D-mannopyranosyl]-α-D-mannopyranosyl;

Y is selected from the group consisting of hydrogen and an amino protecting group; and R represents -A-R₆ radical, wherein A is a methylene radical or a bond directly connecting the radical R₆ with the carbonyl group, and wherein R₆ is phenyl or a napthyl radical, or an acid addition salt thereof.

2. The derivative of claim 1, wherein the phenyl radical is optionally substituted with a substituent selected from the group consisting of methyl, ethyl, methoxy, ethoxy, and phenyl.

3. The derivative of claim 2, wherein A is a methylene radical and R₆ is a phenyl radical substituted with a methyl.

4. The derivative of claim 3, wherein R₆ is 2-methylphenyl.

5. The derivative of claim 1, wherein X is 2-O-α-D-mannopyranosyl-α-D-mannopyranosyl.

6. The derivative of claim 1, wherein Y is hydrogen.

7. A ramoplanin derivative of the formula (f)

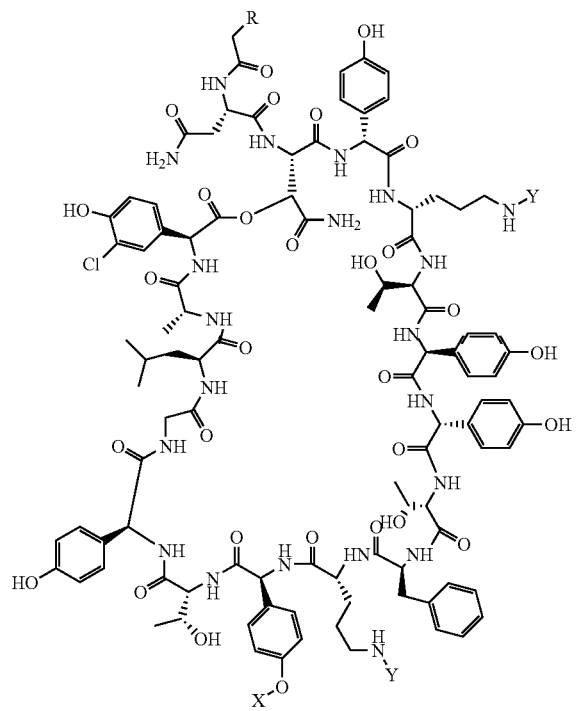

wherein X is selected from the group consisting of hydrogen, 2-α-D-mannopyranosyl, 2-O-α-D-mannopyranosyl-α-D-mannopyranosyl, and 2,3-O-di[α-D-mannopyranosyl]-α-D-mannopyranosyl;

Y is selected from the group consisting of hydrogen and an amino protecting group; and R is a phenyl optionally substituted with a substituent selected from the group consisting of methyl, ethyl, methoxy, ethoxy, and phenyl, or an acid addition salt thereof.

8. The derivative of claim 7, wherein R is 2-methylphenyl.

9. The derivative of claim 7, wherein X is 2-O-α-D-mannopyranosyl-α-D-mannopyranosyl.

10. The derivative of claim 7, wherein Y is hydrogen.

11. A ramoplanin derivative of the formula

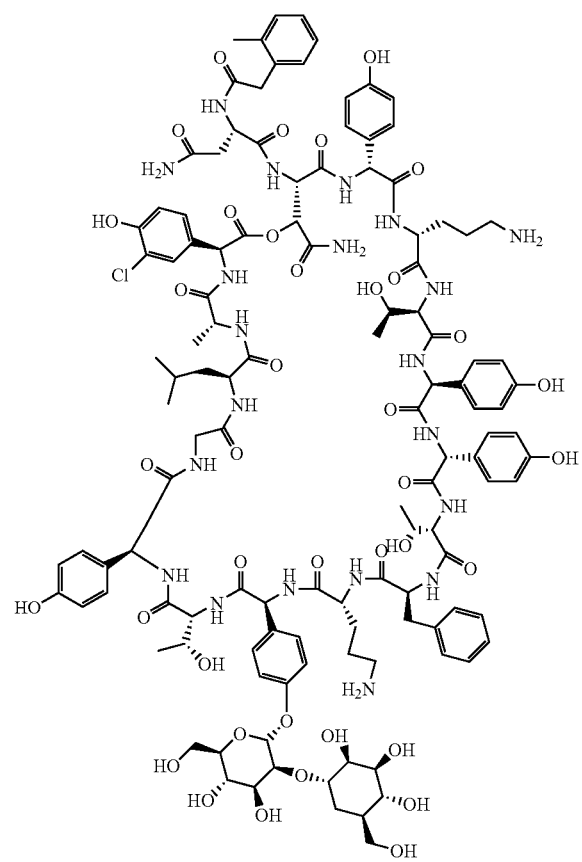

or an acid addition salt thereof.

* * * * *